(12) United States Patent
Bouma et al.

(10) Patent No.: US 7,519,096 B2
(45) Date of Patent: Apr. 14, 2009

(54) PROCESS AND APPARATUS FOR A WAVELENGTH TUNING SOURCE

(75) Inventors: Brett Bouma, Squantum, MA (US);
Seok-Hyun (Andy) Yun, Cambridge, MA (US); Wang-Yuhl (William) Oh, Cambridge, MA (US); Johannes deBoer, Somerville, MA (US); Guillermo Tearney, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 686 days.

(21) Appl. No.: 10/861,179

(22) Filed: Jun. 4, 2004

(65) Prior Publication Data

US 2005/0035295 A1     Feb. 17, 2005

Related U.S. Application Data

(60) Provisional application No. 60/514,769, filed on Oct. 27, 2003, provisional application No. 60/476,600, filed on Jun. 6, 2003.

(51) Int. Cl.
*H01S 3/08* (2006.01)
(52) U.S. Cl. .............................. 372/102; 372/15; 372/24
(58) Field of Classification Search ................ 372/102, 372/50.23, 15, 24
See application file for complete search history.

(56) References Cited

U.S. PATENT DOCUMENTS

| | | | |
|---|---|---|---|
| 2,339,754 A | 1/1944 | Brace | |
| 3,090,753 A | 5/1963 | Matuszak et al. | |
| 3,601,480 A | 8/1971 | Sexton | |
| 3,856,000 A | 12/1974 | Chikama | |
| 3,872,407 A | 3/1975 | Hughes | |
| 3,941,121 A | 3/1976 | Olinger | |
| 3,973,219 A | 8/1976 | Tang et al. | |
| 3,983,507 A | 9/1976 | Tang et al. | |
| 4,030,827 A | 6/1977 | Delhaye et al. | |
| 4,140,364 A | 2/1979 | Yamashita et al. | |
| 4,141,362 A | 2/1979 | Wurster | |

(Continued)

FOREIGN PATENT DOCUMENTS

DE        4105221        9/1991

(Continued)

OTHER PUBLICATIONS

"High Resolution in Vivo Intra-Arterial Imaging with Optical Coherence Tomography" by Jujimoto et al., in the *Official Journal of the British Cardiac Society*, vol. 82, pp. 128-133 Heart—1999.

(Continued)

*Primary Examiner*—Dung T Nguyen
(74) *Attorney, Agent, or Firm*—Dorsey & Whitney LLP

(57) ABSTRACT

An apparatus and source arrangement for filtering an electromagnetic radiation can be provided which may include at least one spectral separating arrangement configured to physically separate one or more components of the electromagnetic radiation based on a frequency of the electromagnetic radiation. The apparatus and source arrangement may also have at least one continuously rotating optical arrangement which is configured to receive at least one signal that is associated with the one or more components. Further, the apparatus and source arrangement can include at least one beam selecting arrangement configured to receive the signal.

24 Claims, 16 Drawing Sheets

U.S. PATENT DOCUMENTS

| | | | |
|---|---|---|---|
| 4,224,929 A | | 9/1980 | Furihata |
| 4,295,738 A | | 10/1981 | Meltz et al. |
| 4,300,816 A | | 11/1981 | Snitzer et al. |
| 4,303,300 A | | 12/1981 | Pressiat et al. |
| 4,428,643 A | * | 1/1984 | Kay ............................ 359/18 |
| 4,479,499 A | | 10/1984 | Alfano |
| 4,533,247 A | | 8/1985 | Epworth |
| 4,585,349 A | | 4/1986 | Gross et al. |
| 4,601,036 A | | 7/1986 | Faxvog et al. |
| 4,607,622 A | | 8/1986 | Fritch et al. |
| 4,631,498 A | | 12/1986 | Cutler |
| 4,650,327 A | | 3/1987 | Ogi |
| 4,744,656 A | | 5/1988 | Moran et al. |
| 4,751,706 A | | 6/1988 | Rohde et al. |
| 4,770,492 A | | 9/1988 | Levin et al. |
| 4,834,111 A | | 5/1989 | Khanna et al. |
| 4,868,834 A | | 9/1989 | Fox et al. |
| 4,890,901 A | | 1/1990 | Cross, Jr. |
| 4,892,406 A | | 1/1990 | Waters |
| 4,909,631 A | | 3/1990 | Tan et al. |
| 4,925,302 A | | 5/1990 | Cutler |
| 4,928,005 A | | 5/1990 | Lefèvre et al. |
| 4,965,441 A | | 10/1990 | Picard |
| 4,965,599 A | * | 10/1990 | Roddy et al. ................. 347/240 |
| 4,993,834 A | | 2/1991 | Carlhoff et al. |
| 5,039,193 A | | 8/1991 | Snow et al. |
| 5,040,889 A | | 8/1991 | Keane |
| 5,045,936 A | | 9/1991 | Lobb et al. |
| 5,046,501 A | | 9/1991 | Crilly |
| 5,065,331 A | | 11/1991 | Vachon et al. |
| 5,085,496 A | | 2/1992 | Yoshida et al. |
| 5,120,953 A | | 6/1992 | Harris |
| 5,121,983 A | | 6/1992 | Lee |
| 5,127,730 A | | 7/1992 | Brelje et al. |
| 5,197,470 A | | 3/1993 | Helfer et al. |
| 5,202,745 A | | 4/1993 | Sorin et al. |
| 5,212,667 A | | 5/1993 | Tomlinson et al. |
| 5,214,538 A | | 5/1993 | Lobb |
| 5,228,001 A | * | 7/1993 | Birge et al. .................. 365/215 |
| 5,248,876 A | | 9/1993 | Kerstens et al. |
| 5,262,644 A | | 11/1993 | Maguire |
| 5,291,885 A | | 3/1994 | Taniji et al. |
| 5,293,872 A | | 3/1994 | Alfano et al. |
| 5,293,873 A | | 3/1994 | Fang |
| 5,304,173 A | | 4/1994 | Kittrell et al. |
| 5,304,810 A | | 4/1994 | Amos |
| 5,305,759 A | | 4/1994 | Kaneko et al. |
| 5,317,389 A | | 5/1994 | Hochberg et al. |
| 5,318,024 A | | 6/1994 | Kittrell et al. |
| 5,321,501 A | | 6/1994 | Swanson et al. |
| 5,353,790 A | | 10/1994 | Jacques et al. |
| 5,383,467 A | | 1/1995 | Auer et al. |
| 5,411,016 A | | 5/1995 | Kume et al. |
| 5,419,323 A | | 5/1995 | Kittrell et al. |
| 5,439,000 A | | 8/1995 | Gunderson et al. |
| 5,441,053 A | | 8/1995 | Lodder et al. |
| 5,450,203 A | | 9/1995 | Penkethman |
| 5,454,807 A | | 10/1995 | Lennox et al. |
| 5,459,325 A | | 10/1995 | Hueton et al. |
| 5,459,570 A | | 10/1995 | Swanson et al. |
| 5,465,147 A | | 11/1995 | Swanson |
| 5,486,701 A | | 1/1996 | Norton et al. |
| 5,491,524 A | | 2/1996 | Hellmuth et al. |
| 5,491,552 A | | 2/1996 | Kittrell |
| 5,526,338 A | | 6/1996 | Hasman et al. |
| 5,562,100 A | | 10/1996 | Kittrell et al. |
| 5,565,986 A | | 10/1996 | Knüttel |
| 5,583,342 A | | 12/1996 | Ichie |
| 5,590,660 A | | 1/1997 | MacAulay et al. |
| 5,600,486 A | | 2/1997 | Gal et al. |
| 5,601,087 A | | 2/1997 | Richards-Kortum et al. |
| 5,621,830 A | | 4/1997 | Lucey et al. |
| 5,623,336 A | | 4/1997 | Raab et al. |
| 5,635,830 A | | 6/1997 | Itoh |
| 5,649,924 A | | 7/1997 | Everett et al. |
| 5,697,373 A | | 12/1997 | Gunderson et al. |
| 5,698,397 A | | 12/1997 | Zarling et al. |
| 5,710,630 A | | 1/1998 | Essenpreis et al. |
| 5,716,324 A | | 2/1998 | Toida |
| 5,719,399 A | | 2/1998 | Alfano et al. |
| 5,735,276 A | | 4/1998 | Lemelson |
| 5,740,808 A | | 4/1998 | Panescu et al. |
| 5,748,318 A | | 5/1998 | Maris et al. |
| 5,748,598 A | | 5/1998 | Swanson et al. |
| 5,784,352 A | | 7/1998 | Swanson et al. |
| 5,785,651 A | | 7/1998 | Kuhn et al. |
| 5,795,295 A | | 8/1998 | Hellmuth et al. |
| 5,801,826 A | | 9/1998 | Williams |
| 5,803,082 A | | 9/1998 | Stapleton et al. |
| 5,807,261 A | | 9/1998 | Benaron et al. |
| 5,817,144 A | | 10/1998 | Gregory |
| 5,840,023 A | | 11/1998 | Oraevsky et al. |
| 5,840,075 A | | 11/1998 | Mueller et al. |
| 5,842,995 A | | 12/1998 | Mahadevan-Jansen et al. |
| 5,843,000 A | | 12/1998 | Nishioka et al. |
| 5,843,052 A | | 12/1998 | Benja-Athon |
| 5,847,827 A | | 12/1998 | Fercher |
| 5,862,273 A | | 1/1999 | Pelletier |
| 5,865,754 A | | 2/1999 | Sevick-Muraca et al. |
| 5,867,268 A | | 2/1999 | Gelikonov et al. |
| 5,871,449 A | | 2/1999 | Brown |
| 5,872,879 A | | 2/1999 | Hamm |
| 5,877,856 A | | 3/1999 | Fercher |
| 5,887,009 A | | 3/1999 | Mandella et al. |
| 5,892,583 A | | 4/1999 | Li |
| 5,912,764 A | | 6/1999 | Togino |
| 5,920,373 A | | 7/1999 | Bille |
| 5,920,390 A | | 7/1999 | Farahi et al. |
| 5,921,926 A | | 7/1999 | Rolland et al. |
| 5,949,929 A | | 9/1999 | Hamm |
| 5,951,482 A | | 9/1999 | Winston et al. |
| 5,955,737 A | | 9/1999 | Hallidy et al. |
| 5,956,355 A | | 9/1999 | Swanson et al. |
| 5,968,064 A | | 10/1999 | Selmon et al. |
| 5,975,697 A | | 11/1999 | Podoleanu et al. |
| 5,983,125 A | | 11/1999 | Alfano et al. |
| 5,987,346 A | | 11/1999 | Benaron et al. |
| 5,991,697 A | | 11/1999 | Nelson et al. |
| 5,994,690 A | | 11/1999 | Kulkarni et al. |
| 6,002,480 A | | 12/1999 | Izatt et al. |
| 6,004,314 A | | 12/1999 | Wei et al. |
| 6,006,128 A | | 12/1999 | Izatt et al. |
| 6,010,449 A | | 1/2000 | Selmon et al. |
| 6,014,214 A | | 1/2000 | Li |
| 6,020,963 A | | 2/2000 | Dimarzio et al. |
| 6,033,721 A | | 3/2000 | Nassuphis |
| 6,044,288 A | | 3/2000 | Wake et al. |
| 6,045,511 A | | 4/2000 | Lutz et al. |
| 6,048,742 A | | 4/2000 | Weyburne et al. |
| 6,053,613 A | | 4/2000 | Wei et al. |
| 6,069,698 A | | 5/2000 | Ozawa et al. |
| 6,091,496 A | | 7/2000 | Hill |
| 6,091,984 A | | 7/2000 | Perelman et al. |
| 6,111,645 A | | 8/2000 | Tearney et al. |
| 6,117,128 A | | 9/2000 | Gregory |
| 6,120,516 A | | 9/2000 | Selmon et al. |
| 6,134,003 A | | 10/2000 | Tearney et al. |
| 6,134,010 A | | 10/2000 | Zavislan |
| 6,134,033 A | | 10/2000 | Bergano et al. |
| 6,141,577 A | | 10/2000 | Rolland et al. |
| 6,151,522 A | | 11/2000 | Alfano et al. |
| 6,159,445 A | | 12/2000 | Klaveness et al. |
| 6,160,826 A | | 12/2000 | Swanson et al. |
| 6,161,031 A | | 12/2000 | Hochman et al. |

| | | | | | | |
|---|---|---|---|---|---|---|
| 6,166,373 | A | 12/2000 | Mao | 2001/0047137 A1 | 11/2001 | Moreno et al. |
| 6,174,291 | B1 | 1/2001 | McMahon et al. | 2002/0016533 A1 | 2/2002 | Marchitto et al. |
| 6,175,669 | B1 | 1/2001 | Colston et al. | 2002/0052547 A1 | 5/2002 | Toida |
| 6,185,271 | B1 | 2/2001 | Kinsinger | 2002/0064341 A1 | 5/2002 | Fauver et al. |
| 6,191,862 | B1 | 2/2001 | Swanson et al. | 2002/0076152 A1 | 6/2002 | Hughes et al. |
| 6,193,676 | B1 | 2/2001 | Winston et al. | 2002/0085209 A1 | 7/2002 | Mittleman et al. |
| 6,198,956 | B1 | 3/2001 | Dunne | 2002/0093662 A1 | 7/2002 | Chen et al. |
| 6,201,989 | B1 | 3/2001 | Whitehead et al. | 2002/0122246 A1 | 9/2002 | Tearney et al. |
| 6,208,415 | B1 | 3/2001 | De Boer et al. | 2002/0140942 A1 | 10/2002 | Fee et al. |
| 6,208,887 | B1 | 3/2001 | Clarke | 2002/0158211 A1 | 10/2002 | Gillispie |
| 6,245,026 | B1 | 6/2001 | Campbell et al. | 2002/0161357 A1 | 10/2002 | Rox et al. |
| 6,249,349 | B1 | 6/2001 | Lauer | 2002/0163622 A1 | 11/2002 | Magnin et al. |
| 6,263,234 | B1 | 7/2001 | Engelhardt et al. | 2002/0172485 A1 | 11/2002 | Keaton et al. |
| 6,264,610 | B1 | 7/2001 | Zhu | 2002/0183623 A1 | 12/2002 | Tang et al. |
| 6,272,376 | B1 | 8/2001 | Marcu et al. | 2002/0188204 A1 | 12/2002 | McNamara et al. |
| 6,274,871 | B1 | 8/2001 | Dukor et al. | 2002/0196446 A1 | 12/2002 | Roth et al. |
| 6,282,011 | B1 | 8/2001 | Tearney et al. | 2002/0198457 A1 | 12/2002 | Tearney et al. |
| 6,297,018 | B1 | 10/2001 | French et al. | 2003/0023153 A1 | 1/2003 | Izatt et al. |
| 6,308,092 | B1 | 10/2001 | Hoyns | 2003/0026735 A1 | 2/2003 | Nolte et al. |
| 6,324,419 | B1 | 11/2001 | Guzelsu et al. | 2003/0028114 A1 | 2/2003 | Casscells III et al. |
| 6,341,036 | B1 | 1/2002 | Tearney et al. | 2003/0082105 A1 | 5/2003 | Fischman et al. |
| 6,353,693 | B1 | 3/2002 | Kano et al. | 2003/0097048 A1 | 5/2003 | Ryan et al. |
| 6,359,692 | B1 | 3/2002 | Groot | 2003/0108911 A1 | 6/2003 | Klimant et al. |
| 6,377,349 | B1 | 4/2002 | Fercher | 2003/0135101 A1 | 7/2003 | Webler |
| 6,384,915 | B1 | 5/2002 | Everett et al. | 2003/0164952 A1 | 9/2003 | Deichmann et al. |
| 6,393,312 | B1 | 5/2002 | Hoyns | 2003/0171691 A1 | 9/2003 | Casscells, III et al. |
| 6,394,964 | B1 | 5/2002 | Sievert, Jr. et al. | 2003/0199769 A1 | 10/2003 | Podoleanu et al. |
| 6,421,164 | B2 | 7/2002 | Tearney et al. | 2003/0216719 A1 | 11/2003 | Debenedictis et al. |
| 6,445,485 | B1 | 9/2002 | Frigo et al. | 2003/0220749 A1 | 11/2003 | Chen et al. |
| 6,445,944 | B1 | 9/2002 | Ostrovsky | 2003/0236443 A1 | 12/2003 | Cespedes et al. |
| 6,459,487 | B1 | 10/2002 | Chen et al. | 2004/0002650 A1 | 1/2004 | Mandrusov et al. |
| 6,463,313 | B1 | 10/2002 | Winston et al. | 2004/0054268 A1 | 3/2004 | Esenaliev et al. |
| 6,469,846 | B2 | 10/2002 | Ebizuka et al. | 2004/0072200 A1 | 4/2004 | Rigler et al. |
| 6,475,159 | B1 | 11/2002 | Casscells et al. | 2004/0077949 A1 | 4/2004 | Blofgett et al. |
| 6,475,210 | B1 | 11/2002 | Phelps et al. | 2004/0086245 A1 | 5/2004 | Farroni et al. |
| 6,485,413 | B1 | 11/2002 | Boppart et al. | 2004/0100631 A1 | 5/2004 | Bashkansky et al. |
| 6,485,482 | B1 | 11/2002 | Belef | 2004/0100681 A1 | 5/2004 | Bjarklev et al. |
| 6,501,551 | B1 | 12/2002 | Tearney et al. | 2004/0126048 A1 | 7/2004 | Dave et al. |
| 6,501,878 | B2 | 12/2002 | Hughes et al. | 2004/0133191 A1 | 7/2004 | Momiuchi et al. |
| 6,538,817 | B1 | 3/2003 | Farmer et al. | 2004/0150829 A1 | 8/2004 | Koch et al. |
| 6,549,801 | B1 | 4/2003 | Chen et al. | 2004/0152989 A1 | 8/2004 | Puttappa et al. |
| 6,552,796 | B2 | 4/2003 | Magnin et al. | 2004/0166593 A1 | 8/2004 | Nolte et al. |
| 6,556,305 | B1 | 4/2003 | Aziz et al. | 2004/0212808 A1 | 10/2004 | Okawa et al. |
| 6,556,853 | B1 | 4/2003 | Cabib et al. | 2004/0239938 A1 | 12/2004 | Izatt |
| 6,558,324 | B1 | 5/2003 | Von Behren et al. | 2004/0263843 A1 | 12/2004 | Knopp et al. |
| 6,564,087 | B1 | 5/2003 | Pitris et al. | 2005/0018201 A1 | 1/2005 | De Boer |
| 6,564,089 | B2 | 5/2003 | Izatt et al. | 2005/0035295 A1 | 2/2005 | Bouma et al. |
| 6,615,071 | B1 | 9/2003 | Casscells, III et al. | 2005/0046837 A1 | 3/2005 | Izumi et al. |
| 6,622,732 | B2 | 9/2003 | Constantz | 2005/0075547 A1 | 4/2005 | Wang |
| 6,680,780 | B1 | 1/2004 | Fee | 2005/0083534 A1 | 4/2005 | Riza et al. |
| 6,685,885 | B2 | 2/2004 | Nolte et al. | 2005/0165303 A1 | 7/2005 | Kleen et al. |
| 6,687,007 | B1 | 2/2004 | Meigs | 2005/0171438 A1 | 8/2005 | Chen et al. |
| 6,687,010 | B1 | 2/2004 | Horii et al. | 2006/0103850 A1 | 5/2006 | Alphonse et al. |
| 6,687,036 | B2 * | 2/2004 | Riza ............ 359/204 | 2006/0146339 A1 | 7/2006 | Fujita et al. |
| 6,701,181 | B2 | 3/2004 | Tang et al. | 2006/0155193 A1 | 7/2006 | Leonardi et al. |
| 6,738,144 | B1 | 5/2004 | Dogariu et al. | 2006/0244973 A1 | 11/2006 | Yun et al. |
| 6,741,355 | B2 | 5/2004 | Drabarek | 2007/0019208 A1 | 1/2007 | Toida et al. |
| 6,790,175 | B1 | 9/2004 | Furusawa et al. | 2007/0291277 A1 | 12/2007 | Everett et al. |
| 6,806,963 | B1 | 10/2004 | Wälti et al. | | | |
| 6,816,743 | B2 | 11/2004 | Moreno et al. | | | |
| 6,839,496 | B1 | 1/2005 | Mills et al. | | | |
| 6,903,820 | B2 | 6/2005 | Wang | | | |
| 6,949,072 | B2 | 9/2005 | Furnish et al. | | | |
| 6,980,299 | B1 | 12/2005 | de Boer | | | |
| 7,006,231 | B2 | 2/2006 | Ostrovsky et al. | | | |
| 7,061,622 | B2 | 6/2006 | Rollins et al. | | | |
| 7,190,464 | B2 | 3/2007 | Alphonse | | | |
| 7,231,243 | B2 | 6/2007 | Tearney et al. | | | |
| 7,242,480 | B2 | 7/2007 | Alphonse | | | |
| 7,355,716 | B2 | 4/2008 | De Boer et al. | | | |
| 7,359,062 | B2 | 4/2008 | Chen et al. | | | |
| 7,366,376 | B2 | 4/2008 | Shishkov et al. | | | |
| 7,391,520 | B2 | 6/2008 | Zhou et al. | | | |

FOREIGN PATENT DOCUMENTS

| | | |
|---|---|---|
| DE | 4309056 | 9/1994 |
| DE | 19542955 | 5/1997 |
| DE | 10351319 | 6/2005 |
| EP | 0110201 | 6/1984 |
| EP | 0251062 | 1/1988 |
| EP | 0617286 | 2/1994 |
| EP | 0590268 | 4/1994 |
| EP | 0728440 | 8/1996 |
| EP | 0933096 | 8/1999 |
| EP | 1324051 | 7/2003 |
| EP | 1426799 | 6/2004 |
| GB | 1257778 | 12/1971 |

| | | |
|---|---|---|
| GB | 2030313 | 4/1980 |
| GB | 2209221 | 5/1989 |
| JP | 4135550 | 5/1992 |
| JP | 4135551 | 5/1992 |
| WO | 7900841 | 10/1979 |
| WO | 9216865 | 10/1992 |
| WO | 9219930 | 11/1992 |
| WO | 9303672 | 3/1993 |
| WO | 9216865 | 10/1993 |
| WO | 9533971 | 12/1995 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 1998048846 | 11/1998 |
| WO | 9905487 | 2/1999 |
| WO | 9944089 | 9/1999 |
| WO | 9957507 | 11/1999 |
| WO | 0058766 | 10/2000 |
| WO | 0108579 | 2/2001 |
| WO | 0138820 | 5/2001 |
| WO | 0142735 | 6/2001 |
| WO | 0236015 | 5/2002 |
| WO | 0238040 | 5/2002 |
| WO | 02054027 | 7/2002 |
| WO | 03020119 | 3/2003 |
| WO | 03052478 | 6/2003 |
| WO | 03062802 | 7/2003 |
| WO | 2003105678 | 12/2003 |
| WO | 2004034869 | 4/2004 |
| WO | 2004066824 | 8/2004 |
| WO | 2004088361 | 10/2004 |
| WO | 2004105598 | 12/2004 |
| WO | 2005000115 | 1/2005 |
| WO | 2005054780 | 6/2005 |
| WO | 2005082225 | 9/2005 |
| WO | 2006014392 | 2/2006 |
| WO | 2006039091 | 4/2006 |
| WO | 2006059109 | 6/2006 |
| WO | 2006130797 | 12/2006 |
| WO | 2007028531 | 3/2007 |
| WO | 2007038787 | 4/2007 |
| WO | 2007083138 | 7/2007 |

OTHER PUBLICATIONS

"Optical Coherence Tomography" by D. Huang et al., in *Science*, vol. 254, pp. 1178-1181, Nov. 1991.

"High-Speed Phase -and Group Delay Scanning with a Grating Based Phase Control Delay Line" by Tearney, et al., in *Optics Letters*, vol. 22, pp. 1811-1813, Dec. 1997.

"In Vivo Video Rate Optical Coherence Tomography" by Rollins, et al., in the *Optics Express*, vol. 3, pp. 219-229, Sep. 1998.

High Speed Fiber-Based Polarization-Sensitive Optical Coherence Tomography of in Vivo Human Skin by Saxer, et al., in the *Optical Society of America*, vol. 25, pp. 1355-1357, Sep. 2000.

"3000 Times Grating Compress or with Positive Group Velocity Dispersion" by Oscar Eduardo Martinez, in the *IEEE*, vol. QE-23, pp. 59-64, Jan. 1987.

"Image Enhancement in Optical Coherence Tomography Using Deconvolution" byKulkarni, et al., in the *Electronics Letters*, vol. 33, pp. 1365-1367, Jul. 1997.

"Signal Processing for Improving Field Cross-Correlation Function in Optical Coherence Tomography" by Bashkansky, et al., in the *Optics & Photonics News*, vol. 9, pp. 8137-8138, May 1998.

"Phase-Domain Processing of Optical Coherence Tomography Images" by Yung, et al., in the *Journal of Biomedical Optics*, vol. 4, pp. 125-136, Jan. 1999.

"In Vivo Endoscopic Optical Biopsy with Optical Coherence Tomography" by Tearney, et al., in the *Science*, vol. 276, Jun. 1997.

"In Vivo Ultrahigh-Resolution Optical Coherence Tomography" by W. Drexler et al., Opt. Lett. vol. 24, pp. 1221-1223, Sep. 1999.

Office Action dated Dec. 6, 2006 for U.S. Appl. No. 10/997,789.

Elliott, K. H. "The use of commercial CCD cameras as linear detectors in the physics undergraduate teaching laboratory", European Journal of Physics 19, 1998, pp. 107-117.

Lauer, V. "New approach to optical diffraction tomography yielding a vector equation of diffraction tomography and a novel tomographic microscope", Journal of Microscopy vol. 205, Issue 2, 2002, pp. 165-176.

Yu, P. et al. "Imaging of tumor necroses using full-frame optical coherence imaging", Proceedings of SPIE vol. 4956, 2003, pp. 34-41.

Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.

Office Action dated Dec. 18, 2006 for U.S. Appl. No. 10/501,276.

Devesa, Susan S. et al. (1998) "Changing Patterns in the Incidence of Esophegeal and Gastric Carcinoma in the United States." *American Cancer Society* vol. 83, No. 10 pp. 2049-2053.

Barr, H et al. (2005) "Endoscopic Therapy for Barrett's Oesophaugs" *Gut* vol. 54:875-884.

Johnston, Mark H.(2005) "Technology Insight: Ablative Techniques for Barrett's Esophagus—Current and Emerging Trends" www.Nature.com/clinicalpractice/gasthep.

Falk, Gary W. et al. (1997) "Surveillance of Patients with Barrett's Esophagus for Dysplasia and Cancer with Ballon Cytology" *Gastroenterology* vol. 112, pp. 1787-1797.

Sepchler, Stuart Jon. (1997) "Barrett's Esophagus: Should We Brush off this Balloning Problem?" *Gastroenterology* vol. 112, pp. 2138-2152.

Froehly, J. et al. (2003) "Multiplexed 3D Imaging Using Wavelength Encoded Spectral Interferometry: A Proof of Principle" *Optics Communications* vol. 222, pp. 127-136.

Kubba A.K. et al. (1999) "Role of p53 Assessment in Management of Barrett's Esophagus" *Digestive Disease and Sciences* vol. 44, No. 4. pp. 659-667.

Reid, Brian J. (2001) "p53 and Neoplastic Progression in Barrett's Esophagus" *The American Journal of Gastroenterology* vol. 96, No. 5, pp. 1321-1323.

Sharma, P. et al.(2003) "Magnification Chromoendoscopy for the Detection of Intestinal Metaplasia and Dysplasia in Barrett's Oesophagus" *Gut* vol. 52, pp. 24-27.

Kuipers E.J et al. (2005) "Diagnostic and Therapeutic Endoscopy" *Journal of Surgical Oncology* vol. 92, pp. 203-209.

Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.

Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.

Canto, Marcia Irene et al (1999) "Vital Staining and Barrett's Esophagus" *Gastrointestinal Endoscopy* vol. 49, No. 3, part 2, pp. 12-16.

Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4, pp. 38-3.

Poneros, John M. et al. (2001) "Diagnosis of Specialized Intestinal Metaplasia by Optical Coherence Tomography" *Gastroenterology* vol. 120, pp. 7-12.

Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.

Brown, Stanley B. et al. (2004) "The Present and Future Role of Photodynamic Therapy in Cancer Treatment" *The Lancet Onocology* vol. 5, pp. 497-508.

Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.

Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.

Sampliner, Richard E. (2004) "Endoscopic Ablative Therapy for Barrett's Esophagus: Current Status" *Gastrointestinal Endoscopy* vol. 59, No. 1, pp. 66-69.

Soetikno, Roy M. et al. (2003) "Endoscopic Mucosal resection" *Gastrointestinal Endoscopy* vol. 57, No. 4, pp. 567-579.

Ganz, Robert A. et al. (2004) "Complete Ablation of Esophageal Epithelium with a Ballon-based Bipolar Electrode: A Phased Evaluation in the Porcine and in Human Esophagus" *Gastrointestinal Endoscopy* vol. 60, No. 6, pp. 1002-1010.

Pfefer, Jorje et al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.

Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.

Vogel, Alfred et al. (2003) "Mechanisms of Pulsed Laser Ablation of Biological Tissues" *American Chemical Society* vol. 103, pp. 577-644.

McKenzie, A. L. (1990) "Physics of Thermal Processes in Laser-Tissue Interaction" *Phys. Med. Biol* vol. 35, No. 9, pp. 1175-1209.

Anderson, R. Rox et al. (1983) "Selective Photothermolysis Precise Microsurgery by Selective Absorption of Pulsed Radiation" *Science* vol. 220, No. 4596, pp. 524-527.

Jacques, Steven L. (1993) "Role of Tissue Optics and Pulse Duration on Tissue Effects During High-Power Laser Irradiation" *Applied Optics* vol. 32, No. 13, pp. 2447-2454.

Nahen, Kester et al. (1999) "Investigations on Acosustic On-Line Monitoring of IR Laser Ablation of burned Skin" *Lasers in Surgery and Medicine* vol. 25, pp. 69-78.

Jerath, Maya R. et al. (1993) "Calibrated Real-Time Control of Lesion Size Based Reflectance Images" *Applied Optics* vol. 32, No. 7, pp. 1200-1209.

Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.

Deckelbaum, Lawrence I. (1994) "Coronary Laser Angioplasty" *Lasers in Surgery and Medicine* vol. 14, pp. 101-110.

Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coagulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Characterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577 nm) Treatment of Port Wine Stains" *Lasers in Surgery and Medicine* vol. 6, pp. 94-99.

French, P.M.W. et al. (1993) "Continuous-wave Mode-Locked $Cr^{4+}$: YAG Laser" *Optics Letters* vol. 18, No. 1, pp. 39-41.

Sennaroglu, Alphan et al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.

Fernández, Cabrera Delia et al. "Automated detection of retinal layer structures on optical coherence tomography images", *Optics Express* vol. 13, No. 25, Oct. 4, 2005, pp. 10200-10216.

Ishikawa, Hiroshi et al. "Macular Segmentation with optical coherence tomography", Investigative Ophthalmology & Visual Science, vol. 46, No. 6, Jun. 2005, pp. 2012-2017.

Office Action dated Aug. 24, 2006 for U.S. Appl. No. 10/137,749.

Barry Cense et al., "Spectral-domain polarization-sensitive optical coherence tomography at 850nm", Coherence Domain Optical Methods and Optical Coherence Tomography in Biomedicine IX, 2005, pp. 159-162.

A. Ymeti et al., "Integration of microfluidics with a four-channel integrated optical Young interferometer immunosensor", Biosensors and Bioelectronics, Elsevier Science Publishers, 2005, pp. 1417-1421.

PCT International Search Report for Applicaiton No. PCT/US2006/018865 filed May 5, 2006.

International Written Opinion for International Patent application No. PCT/US2006/018865 filed May 5, 2006.

John M. Poneros, "Diagnosis of Barrett's esophagus using optical coherence tomography", Gastrointestinal Endoscopy clinics of North America, 14 (2004) pp. 573-588.

P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.

Ko T et al., "Ultrahigh resolution in vivo versus ex vivo OCT imaging and tissue preservation", Conference on Lasers and electro-optics, 2001, pp. 252-253.

Paul M. Ripley et al., "A comparison of Artificial Intelligence techniques for spectral classification in the diagnosis of human pathologies based upon optical biopsy", Journal of Optical Society of America, 2000, pp. 217-219.

Wolfgang Drexler et al., "Ultrahigh-resolution optical coherence tomography", Journal of Biomedical Optics Spie USA, 2004, pp. 47-74.

PCT International Search Report for Application No. PCT/US2006/016677 filed Apr. 28, 2006.

International Written Opinion for International Patent application No. PCT/US2006/016677 filed Apr. 28, 2006.

Office Action dated Nov. 13, 2006 for U.S. Appl. No. 10/501,268.

Office Action dated Nov. 20, 2006 for U.S. Appl. No. 09/709,162.

PCT International Search Report and Written Opinion for Application No. PCT/US2004/023585 filed Jul. 23, 2004.

Marc Nikles et al., "Brillouin gain spectrum characterization in single-mode optical fibers", *Journal of Lightwave Technology* 1997, 15 (10): 1842-1851.

Tsuyoshi Sonehara et al., "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 78 (9): 1667-1670.

K.J. Koski et al., "Brillouin imaging" *Applied Physics Letters* 87, 2005.

Boas et al., "Diffusing temporal light correlation for burn diagnosis" *SPIE*, 1999, 2979:468-477.

David J. Briers, "Speckle fluctuations and biomedical optics: implications and applications", *Optical Engineering*, 1993, 32(2):277-283.

Clark et al., "Tracking Speckle Patterns with Optical Correlation", *SPIE*, 1992, 1772:77-87.

Facchini et al., "An endoscopic system for DSPI", *Optik*, 1993, 95(1):27-30.

Hrabovsky, M., "Theory of speckle dispacement and decorrelation: application in mechanics", *SPIE*, 1998, 3479:345-354.

Sean J. Kirkpatrick et al., "Micromechanical behavior of cortical bone as inferred from laser speckle data", *Journal of Biomedical Materials Research*, 1998, 39(3):373-379.

Sean J. Kirkpatrick et al., "Laser speckle microstrain measurements in vascular tissue", *SPIE*, 1999, 3598:121-129.

Loree et al., "Mechanical Properties of Model Atherosclerotic Lesion Lipid Pools", *Arteriosclerosis and Thrombosis*, 1994, 14(2):230-234.

Podbielska, H. "Interferometric Methods and Biomedical Research", *SPIE*, 1999, 2732:134-141.

Richards-Kortum et al., "Spectral diagnosis of atherosclerosis using an optical fiber laser catheter", *American Heart Journal*, 1989, 118(2):381-391.

Ruth, B. "blood flow determination by the laser speckle method", *Int J Microcirc: Clin Exp*, 1990, 9:21-45.

Shapo et al., "Intravascular strain imaging: Experiments on an Inhomogeneous Phantom", *IEEE Ultrasonics Symposium* 1996, 2:1177-1180.

Shapo et al., "Ultrasonic displacement and strain imaging of coronary arteries with a catheter array", *IEEE Ultrasonics Symposium* 1995, 2:1511-1514.

Thompson et al., "Imaging in scattering media by use of laser speckle", *Opt. Soc. Am. A.*, 1997, 14(9):2269-2277.

Thompson et al., "Diffusive media characterization with laser speckle", *Applied Optics*, 1997, 36(16):3726-3734.

Tuchin, Valery V., "Coherent Optical Techniques for the Analysis of Tissue Structure and Dynamics," *Journal of Biomedical Optics*, 1999, 4(1):106-124.

M. Wussling et al., "Laser diffraction and speckling studies in skeletal and heart muscle", *Biomed, Biochim. Acta*, 1986, 45(1/2):S 23-S 27.

T. Yoshimura et al., "Statistical properties of dynamic speckles", *J. Opt. Soc. Am A.* 1986, 3(7):1032-1054.

Zimnyakov et al., "Spatial speckle correlometry in applications to tissue structure monitoring", *Applied Optics* 1997, 36(22): 5594-5607.

Zimnyakov et al., "A study of statistical properties of partially developed speckle fields as applied to the diagnosis of structural changes in human skin", *Optics and Spectroscopy*, 1994, 76(5): 747-753.

Zimnyakov et al., "Speckle patterns polarization analysis as an approach to turbid tissue structure monitoring", *SPIE* 1999, 2981:172-180.

Ramasamy Manoharan et al., "Biochemical analysis and mapping of atherosclerotic human artery using FT-IR microspectroscopy", *Atherosclerosis*, May 1993, 181-1930.

N.V. Salunke et al., "Biomechanics of Atherosclerotic Plaque" *Critical Reviews™ in Biomedical Engineering* 1997, 25(3):243-285.

Acioli, L. H., M. Ulman, et al. (1991). "Femtosecond Temporal Encoding in Barium-Titanate." *Optics Letters* 16(24): 1984-1986.

Aigouy, L., A. Lahrech, et al. (1999). "Polarization effects in apertureless scanning near-field optical microscopy: an experimental study." *Optical Letters* 24(4): 187-189.

Akiba, M., K. P. Chan, et al. (2003). "Full-field optical coherence tomography by two-dimensional heterodyne detection with a pair of CCD cameras." *Optical Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R.J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of American a-Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3.

Bouma, B. E., M. Ramaswamy-Paye, et al. (1997). "Compact resonator designs for mode-locked solid-state lasers." *Applied Physics B (Lasers and Optics)* B65.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review* E 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3 x 3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micrometer Resolution." *Applied Optics* 26(14): 2836-2842.

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of precancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optical Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo, human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accomodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burn* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burn* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro- Ophthalmology* 18(2): 39-49.

Fercher, A. F., W. Drexler, et al. (1994). *Measurements of optical distances by optical spectrum modulation*. Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry*. Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography*. Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth- scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et al. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd: YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmoloqy & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." *Applied Optics* Draft Copy.

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmoloqv* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated Laser Interferometric Ellipsometry and Precision Reflectometry." *Journal of Physics E-Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmoloqy* 113(8): 1019-29.

Hellmuth, T. and M. Welle (1998). "Simultaneous mesurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micrometer endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with *Retinitis pigmentosa.*" *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N, V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkami, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmoloqy* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." Journal of the *Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "A New Calculus for the Treatment of Optical Systems .8. Electromagnetic Theory." *Journal of the Optical Society of America* 46(2): 126-131.

Jopson, R. M., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomography to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing time." *Burns* 27(4): 359-363.

Knighton, R. W. and X. R. Huang (2002). "Analytical method for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.: Shay, M.; Knutson, Jay R. (1994). "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may by associated with progression from ocular hypertension to primary open angle glaucoma." *Clin Experiment Ophthalmogy* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effects of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utiliization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Opthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth- independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optics Society of America a-Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograh examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics* Part 1-Regular Papers Short Notes & Review Papers 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, Methods, and Baseline Characteristics of Enrolled Patients." *Ophthalmology* 106: 653-662.

Neerken, S., Lucassen, G. W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of Optical Society of America a-Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Semiconductor polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multi-functional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." Ieee Transactions on Microwave Theory and Techniques 47(11): 2075-2084.

Penninckx, D. and V. Morenas (1999). "Jones matrix of polarization mode dispersion." Optics Letters 24(13): 875-877.

Pierce, M. C., M. Shishkov, et al. (2005). "Effects of sample arm motion in endoscopic polarization-sensitive optical coherence tomograpy." Optics Express 13(15): 5739-5749.

Pircher, M., E. Gotzinger, et al. (2003). "Measurement and imaging of water concentration in human cornea with differential absorption optical coherence tomography." Optics Express 11(18): 2190-2197.

Pircher, M., E. Gotzinger, et al. (2003). "Speckle reduction in optical coherence tomography by frequency compounding." Journal of Biomedical Optics 8(3): 565-569.

Podoleanu, A. G., G. M. Dobre, et al. (1998). "En-face coherence imaging using galvanometer scanner modulation." Optics Letters 23(3): 147-149.

Podoleanu, A. G. and D. A. Jackson (1999). "Noise analysis of a combined optical coherence tomograph and a confocal scanning ophthalmoscope." Applied Optics 38(10): 2116-2127.

Podoleanu, A. G., J. A. Rogers, et al. (2000). "Three dimensional OCT images from retina and skin." Optics Express 7(9): 292-298.

Podoleanu, A. G., M. Seeger, et al. (1998). "Transversal and longitudinal images from the retina of the living eye using low coherence reflectometry." Journal of Biomedical Optics 3(1): 12-20.

Poole, C. D. (1988). "Statistical Treatment of Polarization Dispersion in Single-Mode Fiber." Optics Letters 13(8): 687-689.

Povazay, B., K. Bizheva, et al. (2002). "Submicrometer axial resolution optical coherence tomography." Optics Letters 27(20): 1800-1802.

Qi, B., A. P. Himmer, et al. (2004). "Dynamic focus control in high-speed optical coherence tomography based on a microelectromechanical mirror." Optics Communications 232(1-6): 123-128.

Radhakrishnan, S., A. M. Rollins, et al. (2001). "Real-time optical coherence tomography of the anterior segment at 1310 nm." Archives of Ophthalmology 119(8): 1179-1185.

Rogers, A. J. (1981). "Polarization-Optical Time Domain Reflectometry—a Technique for the Measurement of Field Distributions." Applied Optics 20(6): 1060-1074.

Rollins, A. M. and J. A. Izatt (1999). "Optical interferometer designs for optical coherence tomography." Optics Letters 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." Optics Letters 24(19): 1358-1360.

Rollins, A. M., S. Yazdanfar, et al. (2002). "Real-time in vivo colors Doppler optical coherence tomography." Journal of Biomedical Optics 7(1): 123-129.

Rollins, A. M., S. Yazdanfar, et al. (2000). "Imaging of human retinal hemodynamics using color Doppler optical coherence tomography." Investigative Ophthalmology & Visual Science 41(4): S548-S548.

Sandoz, P. (1997). "Wavelet transform as a processing tool in white-light interferometry." Optics Letters 22(14): 1065-1067.

Sankaran, V., M. J. Everett, et al. (1999). "Comparison of polarized-light propagation in biological tissue and phantoms." Optics Letters 24(15): 1044-1046.

Sankaran, V., J. T. Walsh, et al. (2000). "Polarized light propagation through tissue phanto, ehms containing densely packed scatterers." Optics Letters 25(4): 239-241.

Sarunic, M. V., M. A. Choma, et al. (2005). "Instantaneous complex conjugate resolved spectral domain and swept-source OCT using 3x3 fiber couplers." Optics Express 13(3): 957-967.

Sathyam, U. S., B. W. Colston, et al. (1999). "Evaluation of optical coherence quantitation of analytes in turbid media by use of two wavelengths." Applied Optics 38(10): 2097-2104.

Schmitt, J. M. (1997). "Array detection for speckle reduction in optical coherence microscopy." Physics in Medicine and Biology 42(7): 1427-1439.

Schmitt, J. M. (1999). "Optical coherence tomography (OCT): A review." Ieee Journal of Selected Topics in Quantum Electronics 5(4): 1205-1215.

Schmitt, J. M. and A. Knuttel (1997). "Model of optical coherence tomography of heterogeneous tissue." Journal of the Optical Society of America a-Optics Image Science and Vision 14(6): 1231-1242.

Schmitt, J. M., S. L. Lee, et al. (1997). "An optical coherence microscope with enhanced resolving power in thick tissue." Optics Communications 142(4-6): 203-207.

Schmitt, J. M., S. H. Xiang, et al. (1998). "Differential absorption imaging with optical coherence tomography." Journal of the Optical Society of America a-Optics Image Science and Vision 15(9): 2288-2296.

Schmitt, J. M., S. H. Xiang, et aI. (1999). "Speckle in optical coherence tomography." Journal of Biomedical Optics 4(1): 95-105.

Schmitt, J. M., M. J. Yadlowsky, et al. (1995). "Subsurface Imaging of Living Skin with Optical Coherence Microscopy." Dermatology 191(2): 93-98.

Shi, H., Finlay, et al. (1997). "Multiwavelength 10-GHz picosecond pulse generation from a single-stripe semiconductor diode laser." Ieee Photonics Technology Letters 9(11): 1439-1441.

Shi, H., I. Nitta, et al. (1999). "Demonstration of phase correlation in multiwavelength mode-locked semiconductor diode lasers." Optics Letters 24(4): 238-240.

Simon, R. (1982). "The Connection between Mueller and Jones Matrices of Polarization Optics." Optics Communications 42(5): 293-297.

Smith, P. J. M., E.M.; Taylor, C.M.; Selviah, D.R.; Day, S.E.; Commander, L.G. "Variable-Focus Microlenses as a Potential Technology for Endoscopy." no date provided.

Smithies, D. J., T. Lindmo, et al. (1998). "Single attenuation and localization in optical coherence tomography studied by Monte Carlo simulation." Physics in Medicine and Biology 43(10): 3025-3044.

Sorin, W. V. and D. F. Gray (1992). "Simultaneous Thickness and Group Index Measurement Using Optical Low-Coherence Reflectometry." Ieee Photonics Technology Letters 4(1): 105-107.

Sticker, M., C. K. Hitzenberger, et al. (2001). "Quantitative differential phase measurement and imaging in transparent and turbid media by optical coherence tomography." Optics Letters 26(8): 518-520.

Sticker, M., M. Pircher, et al. (2002). "En face imaging of single cell layers by differential phase-contrast optical coherence microscopy." Optics Letters 27(13): 1126-1128.

Stoller, P., B. M. Kim, et al. (2002). "Polarization-dependent optical second-harmonic imaging of a rat-tail tendon." Journal of Biomedical Optics 7(2): 205-214.

Sun, C. S. (2003). "Multiplexing of fiber-optic acoustic sensors in a Michelson interferometer configuration." Optics Letters 28(12): 1001-1003.

Swanson, E. A., J. A. Izatt, et al. (1993). "In-Vivo Retinal Imaging by Optical Coherence Tomography." Optics Letters 18(21): 1864-1866.

Takada, K., A. Himeno, et al. (1991). "Phase-Noise and Shot-Noise Limited Operations of Low Coherence Optical-Time Domain Reflectometry." Applied Physics Letters 59(20): 2483-2485.

Takenaka, H. (1973). "Unified Formalism for Polarization Optics by Using Group-Theory I (Theory)." Japanese Journal of Applied Physics 12(2): 226-231.

Tanno, N., T. Ichimura, et al. (1994). "Optical Multimode Frequency-Domain Reflectometer." Optics Letters 19(8): 587-589.

Tan-no, N., T. Ichimura, et al. (1994). "Optical Multimode Frequency-Domain Reflectometer." Optics Letters 19(8): 587-589.

Targowski, P., M. Wojikowski, et al. (2004). "Complex spectral OCT in human eye imaging in vivo." Optics Communications 229(1-6): 79-84.

Tearney, G. J., S. A. Boppart, et al. (1996). "Scanning single-mode fiber optic catheter- endoscope for optical coherence tomography (vol. 21, p. 543, 1996)." Optics Letters 21(12): 912-912.

Tearney, G. J., B. E. Bouma, et al. (1996). "Rapid acquisition of in vivo biological images by use of optical coherence tomography." Optics Letters 21(17: 1408-1410.

Tearney, G. J., B. E. Bouma, et al. (1997). "In vivo endoscopic optical biopsy with optical coherence tomography." Science 276(5321): 2037-2039.

Tearney, G. J., M. E. Brezinski, et al. (1996). "Catheter-based optical imaging of a human coronary artery." Circulation 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow-velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optical wavelength for ultrahigh-resolution optical coherence tomography." *Optics Express* 11(12): 1411-1417.

Wang, Y. M., Y. H. Zhao, et al. (2003). "Ultrahigh-reslution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

Wojtkowski, M., R. Leitgeb, et al. (2002). "In vivo human retinal imaging by Fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.

Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.

Yabushita, H. B., B.E.; Houser, S.L.; Aretz, H.T.; Jang, I.; Schlendorf, K.H.; Kauffman, C.R.; Shishkov, M.; Halpern, E.F.; Tearney. G.J. "Measurement of Thin Fibrous Caps in Atherosclerotic Plaques by Optical Coherence Tomography." no date provided.

Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz sensitivity applied to the study of cell membrane dynamics." *Optics Letters* 26(16): 1271-1273.

Yang, C. H., A. Wax, et al. (2001). "Phase-dispersion optical tomography." *Optics Letters* 26(10): 686-688.

Yang, C.H., A. Wax, et al. (2000). "Interferometric phase-dispersion microscopy." *Optics Letters* 25(20): 1526-1528.

Yang, V. X. D., M. L. Gordon, et al. (2002). "Improved phase-resolved optical Doppler tolmography using the Kasai velocity estimator and histogram segmentation." Optics Communications 208(4-6): 209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of *Xenopus laevis.*" *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X. D., B. Qi, et al. (2003). "In vivo feasibility of endoscopic catheter-based Doppler optical coherence tomography." *Gastroenterologyv* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-referenced Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13): 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000) "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003), "In vivo imaging of human retinal flow dynamics by color Doppler optical coherence tomography." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength- swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter." *Optics Letters* 28(20): 1981-1983.

Yun, S. H., G. J. Tearney, et al. (2004). "Pulsed-source and swept-source spectral-domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optimal synthesis of several low coherence sources for resolution improvement.", *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. P. Chen, et al. (2000). "Doppler standard deviation imaging for clinical monitoring of in vivo human skin blood flow." *Optics Letters* 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Nicusor V. Iftimia et al., "A Portable, Low Coherence Interferometry Based Instrument for Fine Needle Aspiration Biopsy Guidance" Accepted to Review of Scientific Instruments, 2005.

Abbas, G.L., V.W.S. Chan et al., "Local-Oscillator Excess-Noise Suppression for Homodyne and Heterodyne-Detection", *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers", *Journal Of The Optical Society Of America B-Optical Physics*, vol. 5, pp. 147-159, Jan. 1998.

Andretzky, P. et al., "Optical Coherence Tomography by Spectral Radar: Improvement of Signal-to-Noise Ratio", *The International Society for Optical Engineering*, USA, vol. 3915, 2000.

Ballif, J. et al., "Rapid and Scalable Scans at 21 m/s in optical Low-Coherence Reflectometry", *Optics Letters*, vol. 22, pp. 757-759, Jun. 1997.

Barfuss H. et al., "Modified Optical Frequency-Domain Reflectometry with High Spatial-Resolution for Components of Integrated Optic Systems", *Journal Of Lightwave Technology*, vol. 7, pp. 3-10, Jan. 1989.

Beaud, P. et al., "Optical Reflectometry with Micrometer Resolution for the Investigation of Integrated Optical-Devices", *Ieee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography", *Optics Letters*, vol. 24, pp. 531-533, Apr. 1999.

Brinkmeyer, E. et al., "Efficient Algorithm for Non-Equidistant Interpolation of Sampled Data", *Electronics Letters*, vol. 28, p. 693, Mar. 1992.

Brinkmeyer, E. et al., "High-Resolution OCDR in Dispersive Wave-Guides", *Electronics Letters*, vol. 26, pp. 413-414, Mar. 1990.

Chinn, S.R. et al., "Optical Coherence Tomography Using a Frequency-Tunable Optical Source", *Optics Letters*, vol. 22, pp. 340-342, Mar. 1997.

Danielson, B.L. et al., "Absolute Optical Ranging Using Low Coherence Interferometry", *Applied Optics*, vol. 30, p. 2975, Jul. 1991.

Dorrer, C. et al., "Spectral Resolution and Sampling Issues in Fourier-Transform Spectral Interferometry", *Journal of the Optical Society of America B-Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments", *Optics Express*, vol. 10, p. 1215, Oct. 2002.

Eickhoff, W. et al., "Optical Frequency-Domain Reflectometry in Single-Mode Fiber", *Applied Physics Letters*, vol. 39, pp. 693-695, 1981.

Fercher, Adolf "Optical Coherence Tomography", *Journal of Biomedical Optics*, vol. 1, pp. 157-173, Apr. 1996.

Ferreira, L.A. et al., "Polarization-Insensitive Fiberoptic White-Light Interferometry", *Optics Communications*, vol. 114, pp. 386-392, Feb. 1995.

Fujii, Yohji, "High-Isolation Polarization-Independent Optical Circulator", *Journal of Ligthwave Technology*, vol. 9, pp. 1239-1243, Oct. 1991.

Glance, B., "Polarization Independent Coherent Optical Receiver", *Journal of Lightwave Technology*, vol. LT-5, p. 274, Feb. 1987.

Glombitza, U., "Coherent Frequency-Domain Reflectometry for Characterization of Single-Mode Integrated-Optical Wave-Guides", *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+:Forsterite Laser", *Optics Letters*, vol. 11, pp. 1704-1706, Nov. 1997.

Haberland, U. H. P. et al., "Chirp Optical Coherence Tomography of Layered Scattering Media", *Journal of Biomedical Optics*, vol. 3, pp. 259-266, Jul. 1998.

Hammer, Daniel X. et al., "Spectrally Resolved White-Light Interferometry for Measurement of Ocular Dispersion", *Journal of the Optical Society of America A-Optics Image Science and Vision*, vol. 16, pp. 2092-2102, Sep. 1999.

Harvey, K. C. et al., "External-Cavity Diode-Laser Using a Grazing-Incidence Diffraction Grating", *Optics Letters*, vol. 16, pp. 910-912, Jun. 1991.

Hausler, Gerd et al., "'Coherence Radar' and 'Spectral Radar' New Tools for Dermatological Diagnosis", *Journal of Biomedical Optics*, vol. 3, pp. 21-31, Jan. 1998.

Hee, Michael R. et al., "Polarization-Sensitive Low-Coherence Reflectometer for Birefringence Characterization and Ranging", *Journal of the Optical Society of America B (Optical Physics)*, vol. 9, p. 903-908, Jun. 1992.

Hotate Kazuo et al., "Optical Coherence Domain Reflectometry by Synthesis of Coherence Function", *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplfier", *Applied Physics Letters*, vol. 51, pp. 1051-1053, 1987.

Ivanov, A. P. et al., "New Method for High-Range Resolution Measurements of Light Scattering in Optically Dense Inhomogeneous Media", *Optics Letters*, vol. 1, pp. 226-228, Dec. 1977.

Ivanov, A. P. et al., "Interferometric Study of the Spatial Structure of a Light-Scattering Medium", *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths", *Applied Optics*, vol. 22, pp. 706-710, Mar. 1983.

Kersey, A. D. et al., "Adaptive Polarization Diversity Receiver Configuration for Coherent Optical Fiber Communications", *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm", *Journal of Lightwave Technology*, vol. 9, pp. 1493-1502, Nov. 1991.

Larkin, Kieran G., "Efficient Nonlinear Algorithm for Envelope Detection in White Light Interferometry", *Journal of the Optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography", *Optics Letters*, vol. 25, pp. 820-822, Jun. 2000.

Lexer, F. et al., "Wavelength-Tuning Interferometry of Intraocular Distances", *Applied Optics*, vol. 36, pp. 6548-6553, Sep. 1997.

Mitsui, Takahisa, "Dynamic Range of Optical Reflectometry with Spectral Interferometry", *Japanese Journal of Applied Physics Part 1-Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light", *Optics Letters*, vol. 15, pp. 393-395, Apr. 1990.

Okoshi,Takanori, "Polarization-State Control Schemes for Heterodyne or Homodyne Optical Fiber Communications", *Journal of Lightwave Technology*, vol. LT-3, pp. 1232-1237, Dec. 1995.

Passy, R. et al., "Experimental and Theoretical Investigations of Coherent OFDR with Semiconductor-Laser Sources", *Journal of Lightwave Technology*, vol. 12, pp. 1622-1630, Sep. 1994.

Podoleanu, Adrian G., "Unbalanced Versus Balanced Operation in an Optical Coherence Tomography System", *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier", *Journal of the Optical Society of America B-Optical Physics*, vol. 19, pp. 1286-1294, Jun. 2002.

Schmitt, J. M. et al, "Measurement of Optical-Properties O Biological Tissues By Low-Coherence Reflectometry" *Applied Optics*, vol. 32, pp. 6032-6042, Oct. 1993.

Silberberg, Y. et al., "Passive-Mode Locking of a Semiconductor Diode-Laser", *Optics Letters*, vol. 9, pp. 507-509, Nov. 1984.

Smith, L. Montgomery et al., "Absolute Displacement Measurements Using Modulation of the Spectrum of White-Light in a Michelson Interferometer", *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere", *Applied Optics*, vol. 10, pp. 1600-1604, Jul. 1971.

Sorin, W. V. et al., "Measurement of Rayleigh Backscattering at 1.55 mu m with 32 mu m Spatial Resolution", *IEEE Photonics Technology Letters*, vol. 4, pp. 374-376, Apr. 1992.

Sorin, W. V. et al., "A Simple Intensity Noise-Reduction Technique for Optical Low-Coherence Reflectometry", *IEEE Photonics Technology Letters*, vol. 4, pp. 1404-1406, Dec. 1992.

Swanson, E. A. et al., "High-Speed Optical Coherence Domair Reflectometry", *Optics Letters*, vol. 17, pp. 151-153, Jan. 1992.

Takada, K. et al., "High-Resolution OFDR with Incorporated Fiberoptic Frequency Encoder", *IEEE Photonics Technology Letters*, vol. 4, pp. 1069-1072, Sep. 1992.

"Narrow-Band light Source with Acoustooptic Tunable Filter for Optical Low-Coherence Reflectometry", by Takada, Kazumasa et al., *IEEE Photonics Technology Letters*, vol. 8, pp. 658-660, May 1996.

Takada, Kazumasa et al., "New Measurement System for Fault Location in Optical Wave-Guide Devices Based on an Interometric-Technique", *Applied Optics*, vol. 26, pp. 1603-1606, May 1987.

Tateda, Mitsuhiro et al., "Interferometric Method for Chromatic Dispersion Measurement in a Single-Mode Optical Fiber", *IEEE Journal Of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method", *Applied Physics B (Photophysics and Laser Chemistry)*, vol. B52, pp. 391-394, 1991.

Trutna, W. R. et al., "Continuously Tuned External-Cavity Semiconductor-Laser", *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique", Journal of *Lightwave Technology*, vol. 3, pp. 971-977, Oct. 1985.

Von Der Weid, J. P. et al., "On the Charaterization of Optical Fiber Network Components with Optical Frequency Domain Reflectometry", Journal of *Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M", *Optics Letters*, vol. 15, pp. 879-881, Aug. 1990.

Youngquist, Robert C. et al., "Optical Coherence-Domain Reflectometry—A New Optical Evaluation Technique", *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter", *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser", *Optics Letters*, vol. 23, pp. 843-845, Jun. 1998.

Yung, K. M., "Phase-Domain Processing of Optical Coherence Tomography Images", *Journal of Biomedical Optics*, vol. 4, pp. 125-136, Jan. 1999.

Zhou, Xiao-Qun et al., "Extended-Range FMCW Reflectometry Using an optical Loop with a Frequency Shifter", *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers", *Journal of Lightwave Technology*, vol. 13, pp. 62-66, Jan. 1995.

Victor S. Y. Lin et al., "A Porous Silicon-Based Optical Interferometric Biosensor", *Science*, vol. 278, pp. 840-843, Oct. 31, 1997.

Notice of Reasons for Rejection and English translation for Japanese Patent Application No. 2002-538830.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wang, Xueding et al., "Propagation of Polarized Light in Birefringent Turbid Media: Time-Resolved Simulations," Optical Imaging Laboratory, Biomedical Engineering Program, Texas A&M University, no date provided.

Wong, Brian J.F. et al., "Optical Coherence Tomography of the Rat Cochlea," Journal of *Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang, et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarization-Sensitive Optical Coherence Tomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 µm Wavelength," *Optics Express*, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," 2004, *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.

Huang, Xiang-Run et al., "Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.

Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.

Park, B. Hyle et al., "Comment on Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coherence Tomography Imaging for Dermatology," *The Society for Investigative Dermatology, Inc.* 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging Of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorović, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," *Applied Physics Letters*, vol. 85, No. 15, Oct. 11, 2004, pp. 3023-3025.

D. Fu et al., "Non-invasive quantitative reconstruction of tissue elasticity using an iterative forward approach", *Phys. Med. Biol.* 2000 (45): 1495-1509.

S.B. Adams Jr. et al., "The use of polarization sensitive optical coherence tomography and elastography to assess connective tissue", Optical Soc. of American Washington 2002, p. 3.

International Search Report for International Patent application No. PCT/US2005/039740.

International Written Opinion for International Patent application No. PCT/US2005/039740.

International Search Report for International Patent application No. PCT/US2005/030294.

International Written Opinion for International Patent application No. PCT/US2005/043951.

International Search Report for International Patent application No. PCT/US2005/043951, 2005.

Erdelyi et al. "Generation of diffraction-free beams for applications in optical microlithography", J. Vac. Sci. Technol. B 15 (12), Mar./Apr. 1997, pp. 287-292.

International Search Report for International Patent application No. PCT/US2005/023664, 2005.

International Written Opinion for International Patent application No. PCT/US2005/023664, 2005.

Tearney et al., "Spectrally encoded miniature endoscopy" Optical Society of America; Optical Letters vol. 27, No. 6, Mar. 15 2002; pp. 412-414.

Yelin et al., "Double-clad Fiber for Endoscopy" Optical Society of America; Optical Letters vol. 29, No. 20, Oct. 16, 2005; pp. 2408-2410.

International Search Report for International Patent application No. PCT/US2001/049704, 2001.

International Search Report for International Patent application No. PCT/US2004/039454, 2004.

International Written Opinion for International Patent application No. PCT/US2004/039454, 2004.

PCT International Preliminary Report on Patentability for International Application No. PCT/US2004/038404 dated Jun. 2, 2006.

References cited in Office Action dated Feb. 2, 2007 for U.S. Appl. No. 11/174,425.

References cited in International Search Report PCT/US2006/031905.

References cited in Office Action dated Mar. 28, 2007 for U.S. Appl. No. 11/241,907.

References cited in International Search Report PCT/US2007/060481.

References cited in Office Action dated May 23, 2007 for U.S. Appl. No. 10/406,751.

References cited in Office Action dated May 23, 2007 for U.S. Appl. No. 10/551,735.

References cited in International Search Report PCT/US2007/060717.

References cited in International Search Report PCT/US2007/060319.

References cited in Office Action dated Aug. 10, 2007 for U.S. Appl. No. 10/997,789.

References cited in International Search Report PCT/US2007/060657.

References cited in International Search Report PCT/US2007/061815.

References cited in International Search Report PCT/US2007/062465.

References cited in International Search Report PCT/US2007/066017.

References cited in European Patent Office Search Report for Application No. 01991092.6-2305.

References cited in International Search Report PCT/US2007/060670.

References cited in Office Action dated Oct. 11, 2007 for U.S. Appl. No. 11/534,095.

References cited in Office Action dated Oct. 9, 2007 for U.S. Appl. No. 09/709,162.

References cited in Notice of Allowance dated Oct. 3, 2007 for U.S. Appl. No. 11/225,840.

References cited in Office Action dated Oct. 30, 2007 for U.S. Appl. No. 11/670,069.

Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.

PCT International Search Report and Written Opinion for Application No. PCT/US2006/031905 dated May 3, 2007.

PCT International Search Report and Written Opinion for Application No. PCT/US2007/060481 dated May 23, 2007.

PCT International Search Report and Written Opinion for Application No. PCT/US2007/060717 dated May 24, 2007.

PCT International Search Report and Written Opinion for Application No. PCT/US2007/060319 dated Jun. 6, 2007.

D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., "Applications of Fourier Transform Infrared Imaging Microscopy in Neurotoxicity", Annals New York Academy of Sciences, pp. 234-246, no date provided.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-021006-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006 ∈.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., "Speckle in Optical Coherence Tomography: An Overview", SPIE vol. 3726, pp. 450-461, no date provided.
Office Action dated Oct. 11, 2007, for U.S. Appl. No. 11/534,095.
Office Action dated Oct. 9, 2007, for U.S. Appl. No. 09/709,162.
Notice of Allowance dated Oct. 3, 2007, for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007, for U.S. Appl. No. 11/670,069.
Liptak David C. et al., (2007) "On the Development of a Confocal Rayleigh-Brillouin Microscope" American Institute of Physics vol. 78, 016106.

Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.
Jonathan, Enock (2005) "Dual Reference Arm Low-Coherence Interferometer-Based Reflectometer For Optical Coherence Tomography (OCT) Application" Optics Communications vol. 252.
Motaghian Nezam, S.M.R. (2007) "increased Ranging Depth in optical Frequency Domain Imaging by Frequency Encoding" Optics Letters, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" Applied Physics Letters, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) Optics Letters, Vol. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007 (Oct. 2007), "Abstracts of the 19th Annual Symposium of Transcatheter Cardiovascular Therapeutics, Oct. 20-25, 2007, Washington, DC, USA.".
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. (Oct. 1, "Two-Wavelength Optical Coherence Tomography" Radio physics and Quantum Electronics, Kluwer Academic Publishers-Consultants. vol. 47, No. 10-1. no year provided.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.

Shim M.G. et al., "Study of Fibre-Optic Probes For In vivo Medical Raman Spectroscopy" Applied Spectrscopy. vol. 53, No. 6, Jun. 1999.

Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.

Jun Zhang et al. "Full Range Polarization-Sensitive Fourier Domain Optical Coherence Tomography" Optics Express, vol. 12, No. 24. Nov. 29, 2004.

Yonghua et al., "Real-Time Phase-Resolved Functional Optical Hilbert Transformation" Optics Letters, vol. 27, No. 2, Jan. 15, 2002.

Siavash et al., "Self-Referenced Doppler Optical Coherence Tomography" Optics Letters, vol. 27, No. 23, Dec. 1, 2002.

Tang C.L. et al., "Wide-band electro-optical tuning of semiconductor lasers", Applied Physics Letters, vol. 30, No. 2, Jan. 15, 1977, pp. 113-116.

Tang C. L. et al., "Transient effects in wavelength-modulated dye lasers", Applied Physics Letters, vol. 26, No. 9, May 1, 1975, pp. 534-537.

Telle M. John, et al., "Very rapid tuning of cw dye laser", Applied Physics Letters, vol. 26, No. 10, May 15, 1975, pp. 572-574.

Telle M. John, et al., "New method for electro-optical tuning of tunable lasers", Applied Physics Letters, vol. 24, No. 2, Jan. 15, 1974, pp. 85-87.

Schmitt M. Joseph et al. "OCT elastography: imaging microscopic deformation and strain of tissue", Optics Express, vol. 3, No. 6, Sep. 14, 1998, pp. 199-211.

M. Gualini Muddassir et al., "Recent Advancements of Optical Interferometry Applied to Medicine", IEEE Transactions on Medical Imaging, vol. 23, No. 2, Feb. 2004, pp. 205-212.

Maurice L. Roch et al. "Noninvasive Vascular Elastography: Theoretical Framework", IEEE Transactions on Medical Imaging, vol. 23, No. 2, Feb. 2004, pp. 164-180.

Kirkpatrick J. Sean et al. "Optical Assessment of Tissue Mechanical Properties", Proceedings of the SPIE - The International Society for Optical Engineering SPIE - vol. 4001, 2000, pp. 92-101.

Lisauskas B. Jennifer et al., "Investigation of Plaque Biomechanics from Intravascular Ultrasound Images using Finite Element Modeling", Proceedings of the 19th International Conference - IEEE Oct. 30 - Nov. 2, 1997, pp. 887-888.

Parker K. J. et al., "Techniques for Elastic Imaging: A Review", IEEE Engineering in Medicine and Biology, Nov./Dec. 1996, pp. 52-59.

European Patent Office Search Report for Application No. 05791226.3 no date provided.

Dubois Arnaud et al., "Ultrahigh-resolution OCT using white-light interference microscopy", Proceedings of SPIE, 2003, vol. 4956, pp. 14-21.

Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.

PCT International Search Report and Written Opinion for Application No. PCT/US2007/061463 dated Jan. 23, 2008.

PCT International Search Report and Written Opinion for Application No. PCT/US2007/061481 dated Mar. 17, 2008.

PCT International Search Report and Written Opinion for Application No. PCT/US2007/078254 dated Mar. 28, 2008.

Sadhwani, Ajay et al., "Determination of Teflon thickness with laser speckle I. Potential for burn depth diagnosis", Optical Society of America, 1996, vol. 35, No. 28, pp. 5727-5735.

C.J. Stewart et al., "A comparison of two laser-based methods for determination of burn scar perfusion: Laser Doppler versus laser speckle imaging", Elsevier Ltd., 2005, vol. 31, pp. 744-752.

G. J. Tearney et al., "Atherosclerotic plaque characterization by spatial and temporal speckle pattern analysis", CLEO 2001, vol. 56, pp. 307-307.

PCT International Search Report for Application No. PCT/US2007/068233 dated Feb. 21, 2008.

PCT International Search Report for Application No. PCT/US2007/060787 dated Mar. 18, 2008.

Statement under Article 19 and Reply to PCT Written Opinion for PCT International Application No. PCT/US2005/043951 dated Jun. 6, 2006.

PCT International Preliminary Report on Patentability for Application No. PCT/US2005/043951 dated Jun. 7, 2007.

* cited by examiner

PROCESS AND APPARATUS FOR A WAVELENGTH TUNING SOURCE

CROSS-REFERENCE TO RELATED APPLICATIONS

This application claims priority from U.S. patent application Ser. No. 60/476,600 filed on Jun. 6, 2003, and U.S. patent application Ser. No. 60/514,769 filed on Oct. 27, 2003, the entire disclosure of which is incorporated herein by reference.

STATEMENT REGARDING FEDERALLY SPONSORED RESEARCH

The invention was made with the U.S. Government support under Grant No. DAMD17-99-2-9001 awarded by the U.S. Department of the Army and Grant No. BES-0086789 awarded by the National Science Foundation. Thus, the U.S. Government has certain rights in the invention.

FIELD OF THE INVENTION

The present invention relates generally to optical systems and more particularly to an optical wavelength filter system for wavelength tuning.

BACKGROUND OF THE INVENTION

Considerable effort has been devoted for developing rapidly and widely tunable wavelength laser sources for optical reflectometry, biomedical imaging, sensor interrogation, and tests and measurements. A narrow line width, wide-range and rapid tuning have been obtained by the use of an intra-cavity narrow band wavelength scanning filter. Mode-hopping-free, single-frequency operation has been demonstrated in an extended-cavity semiconductor laser by using a diffraction grating filter design. Obtaining single-frequency laser operation and ensuring mode-hop-free tuning, however, may use a complicated mechanical apparatus and limit the maximum tuning speed. One of the fastest tuning speeds demonstrated so far has been limited less than 100 nm/s. In certain applications such as biomedical imaging, multiple-longitudinal mode operation, corresponding to an instantaneous line width as large or great than 10 GHz, may be sufficientl. Such width may provide a ranging depth of a few millimeters in tissues in optical coherence tomography and a micrometer-level transverse resolution in spectrally-encoded confocal microscopy.

A line width on the order of 10 GHz is readily achievable with the use of an intra-cavity tuning element (such as an acousto-optic filter, Fabry-Perot filter, and galvanometer-driven diffraction grating filter). However, the sweep frequency previously demonstrated has been less than 1 kHz limited by finite tuning speeds of the filters. Higher-speed tuning with a repetition rate greater than 15 kHz may be needed for video-rate (>30 frames/s), high-resolution optical imaging in biomedical applications.

Accordingly, there is a need to overcome the above-described deficiencies.

SUMMARY OF THE INVENTION

According to the exemplary concepts of the present invention, an optical wavelength filter may be provided that can be tuned with a repetition rate of greater than 15 kHz over a wide spectral range. In addition, a wavelength tuning source comprising such optical filter in combination with a laser gain medium may be provided. The tuning source may be useful in video-rate optical imaging applications, such as the optical coherence tomography and spectrally encoded confocal microscope.

In general, the optical filter according to one exemplary embodiment of the present invention may include a diffraction grating, a rotating polygon scanner, and a telescope. Such optical filter can be operated at a tuning speed more than an order of magnitude higher than the conventional filters. The wavelength tunable light source may be implemented by employing the filter, e.g., in combination with a laser gain medium. The filter and gain medium may further, be incorporated into a laser cavity. For example, a laser can emit a narrow band spectrum with its center wavelength being swept over a broad wavelength range at a high repetition rate.

In one exemplary embodiment of the present invention, an apparatus is provided which includes an arrangement for emitting an electromagnetic radiation that has a spectrum whose mean frequency changes substantially continuously over time. Such radiation is may be associated with a tuning speed that is greater than 100 terahertz per millisecond. The mean frequency can change repeatedly at a repetition rate that is greater than 5 kilohertz or over a range greater than 10 terahertz. The spectrum may have a tuning range covering a portion of the visible, near-infrared or infrared wavelengths. Exemplary spectra may be centered at approximately at 850 nm, 1300 nm or 1700 nm wavelengths. Further, the spectrum may have an instantaneous line width that is smaller than 100 gigahertz. The apparatus may also include a laser cavity with a roundtrip length shorter than 5 m. The apparatus may also have a polygon scanner arrangement which may be adapted to receive at least a portion of the emitted electromagnetic radiation and reflect or deflect the portion to a further location. In addition, a beam separating arrangement can be provided which selectively receives components of the electromagnetic radiation.

According to another exemplary embodiment of the present invention the apparatus for filtering an electromagnetic radiation can include at least one spectral separating arrangement configured to physically separate one or more components of the electromagnetic radiation based on a frequency of the electromagnetic radiation. The apparatus may also have at least one continuously rotating optical arrangement that is configured to receive the physically separated components and selectively direct individual components to a beam selecting arrangement.

In one exemplary variation of the present invention, the spectral separating arrangement includes a diffraction grating, a prism, a grism, an acousto-optic beam deflector, a virtual phased array, and/or an arrayed waveguide grating. The continuously rotating optical arrangement may be a polygon mirror, a diffractive element, a substantially opaque disk having an array of substantially transparent regions, and/or a substantially transparent disk having an array of substantially reflective regions. The spectral separating arrangement may also include a holographic grating mounted on a substrate comprising a continuously rotating optical arrangement.

In another exemplary variation of the present invention the beam selecting arrangement may be an optical fiber, an optical waveguide, a pinhole aperture, a combination of a lens with an optical fiber, waveguide or pinhole, and/or a spatial filter. The beam selecting arrangement can include a plurality of beam selecting elements, and the electromagnetic radiation which is transmitted by the plurality of beam selecting elements may be combined. The signal may be reflected multiple times from the continuously rotating optical arrangement before being received by the selecting arrangement.

According to yet another exemplary embodiment of the present invention the apparatus for filtering an electromagnetic radiation may include at least one spectral separating arrangement configured to angularly separate one or more components of the electromagnetic radiation based on a frequency of the electromagnetic radiation. Such arrangement can also include at least one angularly deflecting optical arrangement that includes a pivot point, and that is configured to receive the components of the electromagnetic radiation and selectively direct the components to a beam selecting arrangement. Further, the arrangement can include at least one optical imaging arrangement configured to receive the components of the electromagnetic radiation and generate an image of one or more dispersive elements associated with the components. The position of the pivot point of the angularly deflecting optical arrangement may be provided in proximity to a real or virtual image of at least one of the dispersive elements.

In one exemplary variant of the present invention, a deflection point of the angularly deflecting optical element may substantially overlap with a real image of at least one of the dispersive elements. At least one reflector which is configured to receive at least one signal from the at least one angularly deflecting optical arrangement may also be provided. One or more of the dispersive elements may be a diffraction grating, a prism, a grism, an acousto-optic beam deflector, a virtual phased array, and/or an arrayed waveguide grating. The angularly deflecting optical element may be a polygon mirror scanner, a galvanometer mirror scanner, or a piezo-electric mirror scanner.

According to still another exemplary embodiment of the present invention, an apparatus is provided for filtering an electromagnetic radiation. The apparatus includes at least one dispersive arrangement configured to angularly separate components of the electromagnetic radiation based on a frequency of the electromagnetic radiation, and generate frequency-separated components. The apparatus may also include at least one angularly deflecting optical element having a pivot point of an angular deflection. The pivot point can substantially overlap a location where substantially all of the frequency-separated components overlap.

In another exemplary embodiment of the present invention, at least one spectral separating arrangement can be provided that is configured to physically separate one or more components of the electromagnetic radiation based on a frequency of the electromagnetic radiation. In addition, at least one continuously rotating optical arrangement may be included which is configured to receive at least one signal that is associated with the one or more components. At least one beam selecting arrangement may also be configured to receive the signal. The emitter can be a laser gain medium, a semiconductor optical amplifier, a laser diode, a super-luminescent diode, a doped optical fiber, a doped laser crystal, a doped laser glass, and/or a laser dye.

In still another exemplary embodiment of the present invention, a source arrangement can provide an electromagnetic radiation. The source includes at least one emitter of the electromagnetic radiation, at least one spectral separating arrangement configured to angularly separate one or more components of the electromagnetic radiation based on a frequency of the electromagnetic radiation, as well as at least one angularly deflecting optical arrangement that includes a pivot point, and configured to receive the components of the electromagnetic radiation to generate at least one signal associated with the one or more components. In addition, the source arrangement can include at least one beam selecting arrangement adapted to receive the signal, and selectively generate at least one selected signal, and at least one optical imaging arrangement configured to received the selected signal, and generate an image of one or more dispersive elements associated with the one or more components. In a variation of the present invention, more than one laser gain medium providing electromagnetic radiation and at least one spectral separating arrangement configured to physically separate one or more components of the electromagnetic radiation based on a frequency of the electromagnetic radiation can be provided. In this variation, the selected components of electromagnetic radiation from each laser gain medium are synchronized, and can be used separately or combined.

In one further exemplary embodiment of the present invention, a high-speed tuning of an extended-cavity semiconductor laser may be provided. The laser resonator may include a unidirectional fiber-optic ring, a semiconductor optical amplifier as the gain medium, and a scanning filter based on a polygon scanner. Variable tuning rates of up to 1,150 nm/ms (15.7 kHz repetition frequency) can be obtained over a 70 nm wavelength span centered at 1.32 μm. Such tuning rate can be more than an order of magnitude faster than is conventionally know, and may be facilitated in part by self-frequency shifting in the semiconductor optical amplifier. The instantaneous line width of the source may be <0.1 nm for 9-mW cw output power, and a low spontaneous-emission background of 80 dB can be obtained.

Other features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which.

DETAILED DESCRIPTION

Figure 1A:
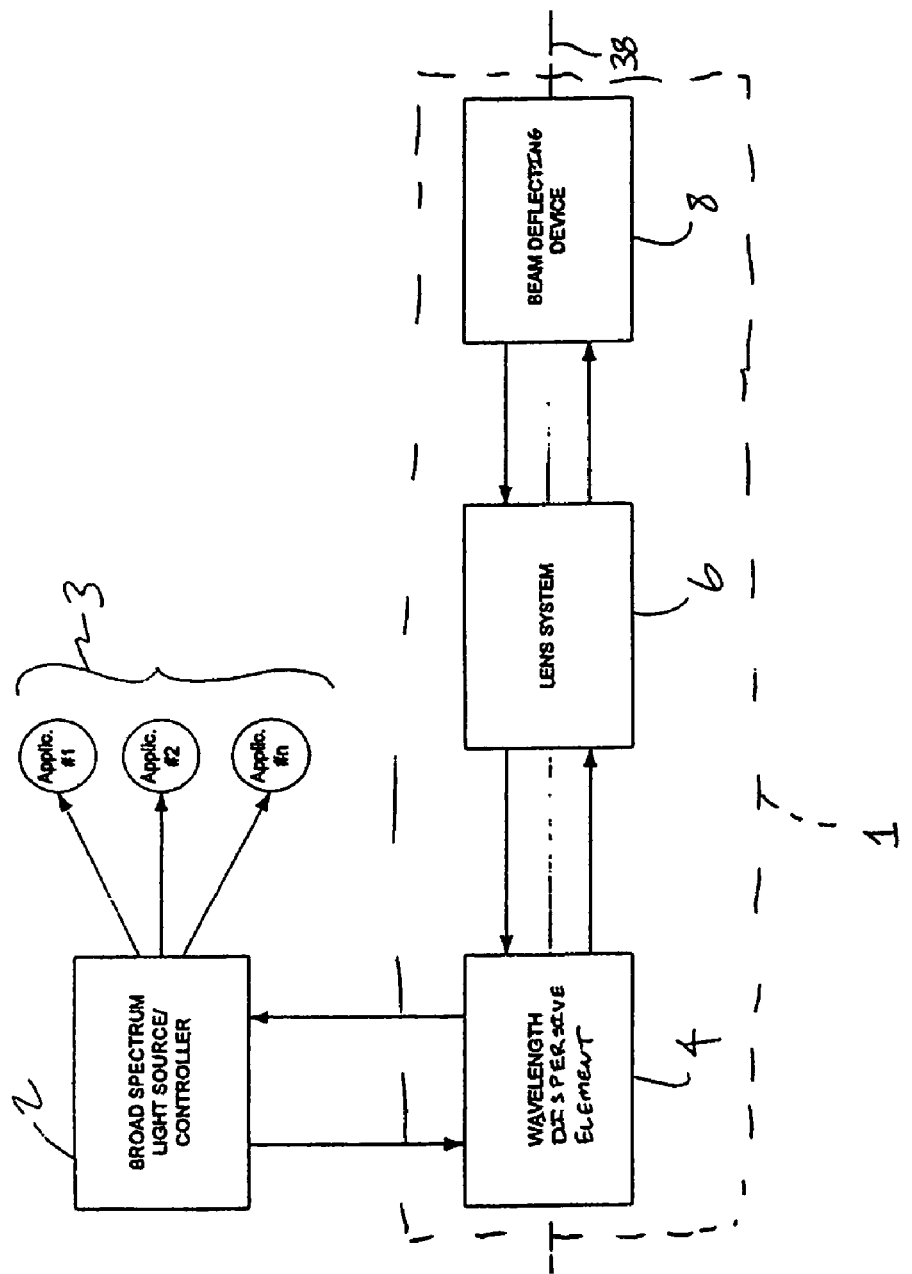
FIG. 1A is a block diagram of a first exemplary embodiment of an optical wavelength filter according to the present invention.

FIG. 1A shows a block diagram of a first exemplary embodiment of an optical wavelength filter 1 in accordance the present invention. In this first exemplary embodiment, the optical wavelength filter 1 can be used in a variety of different applications, general examples of which are described below. In this example, the filter 1 may be coupled to one or more applications 3 via a light source 2. It should be understood that in certain exemplary applications, the filter 1 can be used with or connected to an application (e.g., one or more of the applications 3) via a device other than a light source (e.g. a passive or active optical element). In the first exemplary embodiment shown in FIG. 1A, a broad spectrum light source and/or controller 2 (hereinafter referred to as "light controller"), may be coupled to a wavelength dispersing element 4. The light controller 2 can be further coupled to one or more of the applications 3 that are adapted to perform one or more tasks with or for, including but not limited to, optical imaging processes and optical imaging systems, laser machining processes and systems, photolithography and photolithographic systems, laser topography systems, telecommunications processes and systems, etc . . . The wavelength dispersing element 4 can be coupled to a lens system 6, which is further coupled to a beam deflection device 8.

The light controller 2 can be one or more of various systems and/or arrangements that are configured to transmit a beam of light having a broad frequency (f) spectrum. In one exemplary embodiment, the beam of light may be a collimated beam of light The beam of light can include a plurality of wavelengths λ . . . λn, within the visible light spectrum (e.g., red, blue, green). Similarly, the beam of light provided by the light controller 2 can also include a plurality of wavelengths λ . . . λn that may be defined outside of the visible spectrum (e.g., ultraviolet, near infrared or infrared). In one exemplary embodiment of the present invention, the light controller 2 can include a unidirectional light transmission ring, which shall be described in further detail below in connection with FIG. 3 which shows an exemplary embodiment of a wavelength tuning laser source. Further, in another exemplary embodiment of the present invention, the light controller 2 can include a linear resonator system, which shall be described in further detail below in connection with FIG. 6.

The wavelength dispersing element 4 of the optical wavelength filter 1 can include one or more elements that are specifically adapted to receive the beam of light from the light controller 2, and to conventionally separate the beam of light into a plurality of wavelengths of light having a number of directions. The wavelength dispersing element 4 is further operative to direct portions of light having different wavelengths in equal angular directions or displacements with respect to an optical axis 38. In one exemplary embodiment of the present invention, the wavelength dispersing element 4 can include a light dispersion element, which may include but not limited to, a reflection grating, a transmission grating, a prism, a diffraction grating, an acousto-optic diffraction cell or combinations of one or more of these elements.

The lens system 6 of the optical wavelength filter 1 can include one or more optical elements adapted to receive the separated wavelengths of light from the wavelength dispersing element. Light at each wavelength propagates along a path which is at an angle with respect to the optical axis 38. The angle is determined by the wavelength dispersing element 4. Furthermore, the lens system 6 is adapted to direct or steer and/or focus the wavelengths of light to a predetermined position located on a beam deflection device 8.

The beam deflection device 8 can be controlled to receive and selectively redirect one or more discrete wavelengths of light back along the optical axis 38 through the lens system 6 to the wavelength dispersing element 4 and back to the light controller 2. Thereafter, the light controller 2 can selectively direct the received discrete wavelengths of light to any one or more of the applications. The beam deflecting device 8 can be provided in many different ways. For example, the beam deflecting device 8 can be provided from elements including, but not limited to, a polygonal mirror, a planar mirror disposed on a rotating shaft, a mirror disposed on a galvonmeter, or an acousto-optic modulator.

Figure 1B:
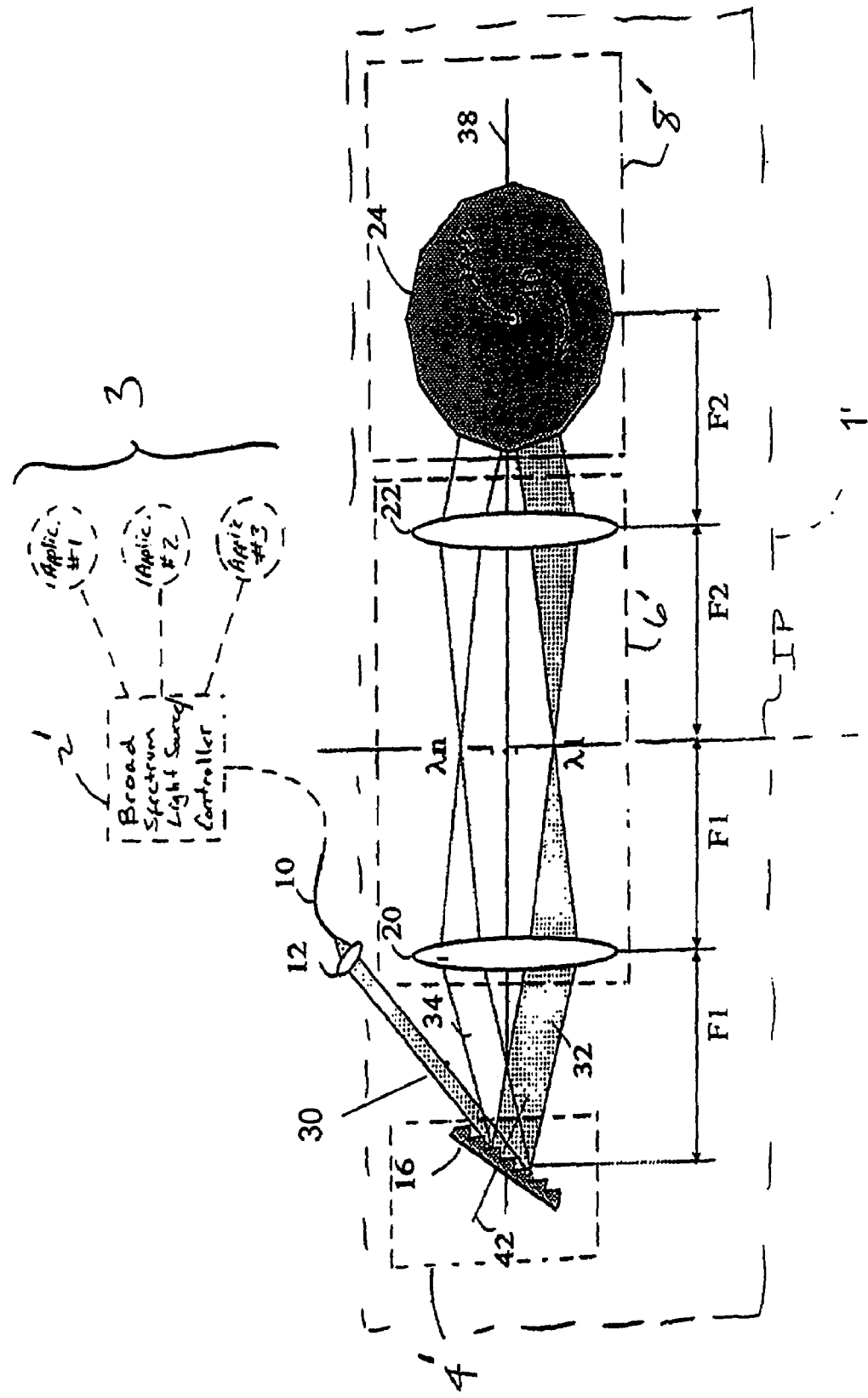
FIG. 1B is a block diagram of a second exemplary embodiment of the optical wavelength filter according to the present invention.

FIG. 1B shows a schematic diagram of a second exemplary embodiment of the optical wavelength filter 1'. The exemplary optical wavelength filter 1' can be configured as a reflection-type filter which may have substantially identical input and output ports. An input/output optical fiber 10 and a collimating lens 12 can provide an input from a light controller 2' (which may be substantially similar to the light controller 2 described above with reference to FIG. 1A) to the optical wavelength filter 1'. The optical wavelength filter 1' includes a diffraction grating 16, optical telescoping elements 6' (hereinafter referred to as "telescope 6'") and may possibly be similar to the lens system 6 of FIG. 1A), and a polygon mirror scanner 24. The telescope 6' can include two lenses, e.g., first and second lenses 20, 22 with 4-f configuration.

In the second exemplary embodiment of the optical wavelength filter 1' shown in FIG. 1B, the telescope 6' includes the first and second lenses 20, 22, which are each substantially centered along the optical axis 38. The first lens 20 may be located at a first distance from the wavelength dispensing element 4' (e.g., diffraction grating 16), which can approximately be equal to the focal length F1 of the first lens 20. The second lens 22 may be located at a second distance from the first lens 20, which can be approximately equal to the sum of the focal length F1 of the first lens 20 and the focal length F2 of the second lens 22. Using such arrangement, the first lens 20 can receive one or more collimated discrete wavelengths of light from the wavelength dispersing element 4', and can effectively perform a Fourier Transform on each one of the collimated one or more discrete wavelengths of light to provide one or more approximately equal converging beams that are projected onto an image plane IP.

The image plane IP is preferably located between the first lens 20 and the second lens 22 and at a predetermined distance from the first lens 20. According to one exemplary variation of the present invention, such predetermined distance may be defined by the focal length F1 of the first lens 20. After such one or more converging beams are propagated through the image plane IP, these one or more converging beams form equal or corresponding one or more diverging beams that are received by the second lens 22. The second lens 22 is adapted to receive the diverging beams and provide approximately an equal number of collimated beams having predetermined angular displacements with respect to the optical axis 38. Thus, the second lens 22 can direct or steer the collimated beams to predefined portions of the beam deflection device 8'.

The telescope 6' according to the second exemplary embodiment of the present invention is operative to provide one or more features as described above, as well as to convert a diverging angular dispersion from the grating into converging angular dispersion after the second lens 22. Such result may be advantageous for a proper operation of the filter. In addition, the telescope 6' may provide adjustable parameters which control the tuning range and linewidth and reduce the beam size at the polygon mirror to avoid beam clipping. As is illustrated in the exemplary embodiment of FIG. 1B, a beam deflection device 6' (e.g., which may include a polygon mirror or arrangement 24) is adapted to preferably reflect back only the spectral component within a narrow passband as a function of the angle of the front mirror facet of the polygon arrangement 24 with respect to the optic axis 38. The reflected narrow band light is diffracted and received by the optical fiber 10. The orientation of the incident beam 30 with respect to the optic axis and a rotation direction 40 of the polygon arrangement 24 can be used to determine the direction of wavelength tuning, e.g., a wavelength up (positive) scan or a wavelength down (negative) scan. The exemplary arrangement shown in FIG. 1B can generate a positive wavelength sweep. It should be understood that although the polygon arrangement 24 is shown in FIG. 1B as having twelve facets, polygon arrangements which have fewer than twelve facets or greater than twelve facets can also be used. While generally not considering practical mechanical limits, based upon conventional manufacturing techniques, a particular number of facets of the polygon arrangement 24 to use in any application may depend on a desired scanning rate and a scanning range for a particular application.

Furthermore, the size of the polygon arrangement 24 may be selected based on preferences of a particular application, and preferably taking into account certain factors including, but not limited to, manufacturability and weight of the polygon arrangement 24. It should also be understood that lenses 20, 22 that have different focal lengths may be provided. For example, the lenses 20, 22 should be selected to provide a focal point at approximately the center point 24a of the polygon arrangement 24.

In one exemplary embodiment, a Gaussian beam 30 can be utilized with a broad optical spectrum incident to the grating from the fiber collimator 12. The well-known grating equation is expressed as $\lambda = p \cdot (\sin \alpha + \sin \beta)$ where $\lambda$ is the optical wavelength, p is the grating pitch, and $\alpha$ and $\beta$ are the incident and diffracted angles of the beam with respect to the normal axis 42 of the grating, respectively. The center wavelength of tuning range of the filter may be defined by $\lambda_0 = p \cdot (\sin \alpha + \sin \beta_0)$ where $\beta_0$ is the angle between the optic axis 38 of the telescope and the grating normal axis. FWHM bandwidth of the filter is defined by $(\delta\lambda)_{FWHM}/\lambda_0 = A \cdot (p/m) \cos \alpha / W$, where $A = \sqrt{4\ln2}/\pi$ for double pass, m is the diffraction order, and W is $1/e^2$-width of the Gaussian beam at the fiber collimator.

Tuning range of the filter may be limited by the finite numerical aperture of the first lens 20. The acceptance angle of the first lens 20 without beam clipping may be defined by $\Delta\beta = (D_1 - W \cos \beta_0 / \cos \alpha)/F_1$, where $D_1$ and $F_1$ are the diameter and focal length of the first lens 20. Such formulation relates to the filter tuning range via $\Delta\lambda = p \cos \beta_0 \cdot \Delta\beta$. One of exemplary design parameters of the filter, originated from the multiple facet nature of the polygon mirror, is the free spectral range, which is described in the following. A spectral component after propagating through the first lens 20 and the second lens 22 may have a beam propagation axis at an angle $\beta'$ with respect to the optic axis 38, e.g., $\beta' = -(\beta-\beta_0) \cdot (F_1/F_2)$, where $F_1$ and $F_2$ are the focal lengths of the first lens 20 and the second lens 22, respectively. The polygon arrangement 24 may have a facet-to-facet polar angle given by $\theta = 2\pi/N \approx L/R$, where L is the facet width, R is the radius of the polygon and N is the number of facets. If the range of $\beta'$ of incident spectrum is greater than the facet angle, i.e. $\Delta\beta' = \Delta\beta \cdot (F_1/F_2) > \theta$, the polygon arrangement 24 can retro-reflect more than one spectral component at a given time. The spacing of the multiple spectral components simultaneously reflected, or the free spectral range, can be defined as $(\Delta\lambda)_{FSR} = p \cos \beta_0 (F_1/F_2) \cdot \theta$. In an exemplary intra-cavity scanning filter application, the free spectral range of the filter should exceed the spectral range of the gain medium in order to avoid multiple frequency bands (in the case of an inhomogeneously broadened gain medium) or limited tuning range (in the case of a homogeneously broadened gain medium).

The duty cycle of laser tuning by the filter can be, for example, 100% with no excess loss caused by beam clipping if two preferable conditions are met as follows:

$$W < \frac{\cos\alpha}{\cos\beta} \frac{F_1}{F_2} L \text{ and } W < \frac{\cos\alpha}{\cos\beta_0}(F_2 - S) \cdot \theta \qquad (1)$$

The first equation may be derived from a condition that the beam width after the second lens 22 should be smaller than the facet width. The second equation can be derived from that the two beams at the lowest 32 and highest wavelengths 34 of the tuning range, respectively, which should not overlap each other at the polygon arrangement 24. S in equation (1) denotes the distance between the second lens 22 and the front mirror of the polygon arrangement 24.

It is possible to select the optical components with the following parameters: W=2.4 mm, p=1/1200 mm, $\alpha$=1.2 rad, $\beta_0$=0.71 rad, m=1, $D_1$=$D_2$=25 mm, $F_1$=100 mm, $F_2$=45 mm, N=24, R=25 mm, L=6.54, S=5 mm, $\theta$=0.26 rad, $\lambda_0$=1320 nm. From the parameters, the theoretical FWHM bandwidth, tuning range and free spectral range of the filter could be calculated: $(\delta\lambda)_{FWHM}$=0.09 nm, $\Delta\lambda$=126 nm and $(\Delta\lambda)_{FSR}$=74 nm. Both conditions in equation (1) may be satisfied with particular margins.

Figure 1C:
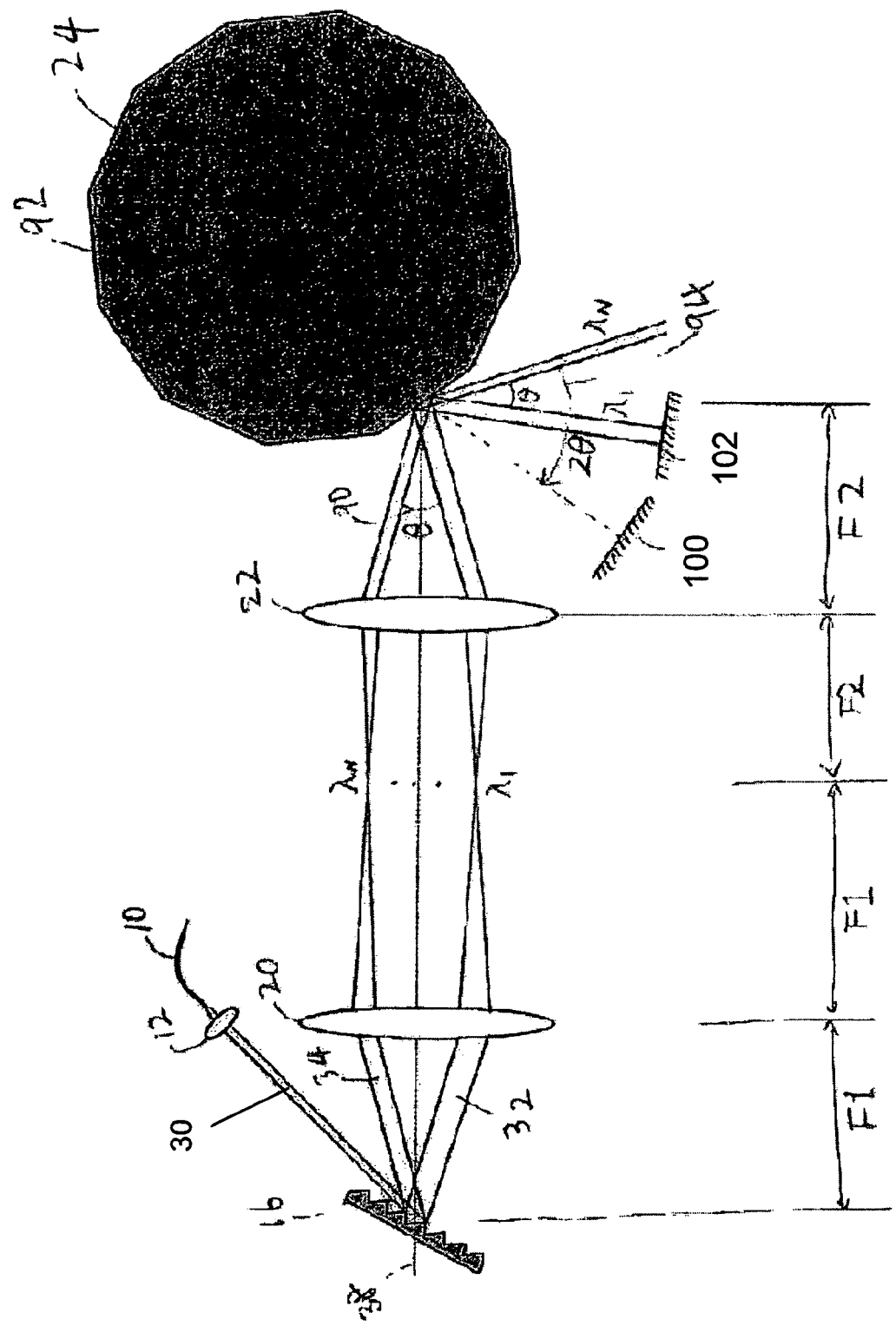
FIG. 1C is a block diagram of a third exemplary embodiment of the optical wavelength filter according to the present invention.

FIG. 1C shows a diagram of a third exemplary embodiment of the wavelength tunable filter arrangement for doubling the tuning speed with the same polygon rotation speed according to the present invention. In this exemplary embodiment, the mirror surface of the polygon arrangement 24 is placed substantially a distance F2 from lens 22, and the beam of light is reflected with a non-zero angle (rather than directly being reflected back to the telescope from the polygon arrangement's 24 mirror facet). The sweep angle of the reflected light from the polygon arrangement 24 is double the polygon arrangement's 24 rotation angle. When the incident angle difference 90 between $\lambda_1$ and $\lambda_N$ with respect to the polygon arrangement 24 is approximately the same as the facet-to-facet angle 92 of the polygon, e.g., angle θ, the sweep angle 94 of the reflected light is 2θ for a rotation of the angle θ of the polygon arrangement 24. By placing two reflectors 100, 102, which preferably direct the reflected beam of light from the polygon arrangement 24 back to the polygon arrangement 24, and to the telescope (e.g., similar to the telescope 6' of FIG. 1B), with the angle θ between each other, twice wavelength scans from $\lambda_1$ to $\lambda_N$ are achieved for the polygon rotation of the one facet-to-facet angle θ.

Figure 1D:
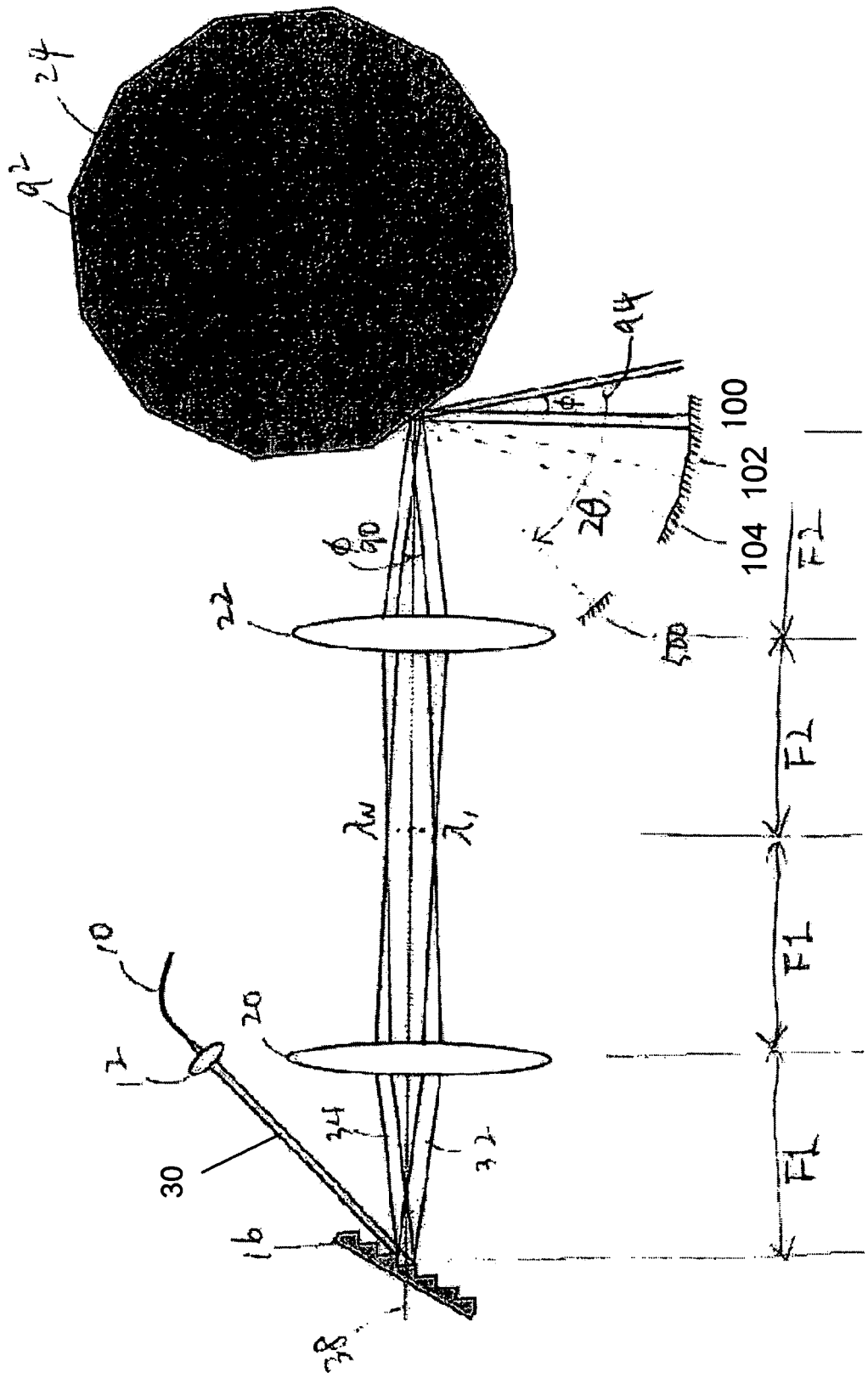
FIG. 1D is a block diagram of a fourth exemplary embodiment of the optical wavelength filter according to the present invention.

In FIG. 1D which shows a fourth exemplary embodiment of the present invention, the incident angle 90 difference between $\lambda_1$ and $\lambda_N$ to the polygon arrangement 24 is smaller than polygon facet-to facet angle 92, e.g., φ(=θ/K, where K>1). This can be achieved by reducing the grating pitch and increasing the F2/F1 ratio. In this exemplary embodiment, the filter tuning speed may be increased by factor of 2K without increasing either the rotation speed of the polygon arrangement 24 or the number of facets of the polygon arrangement 24.

Figure 1E:
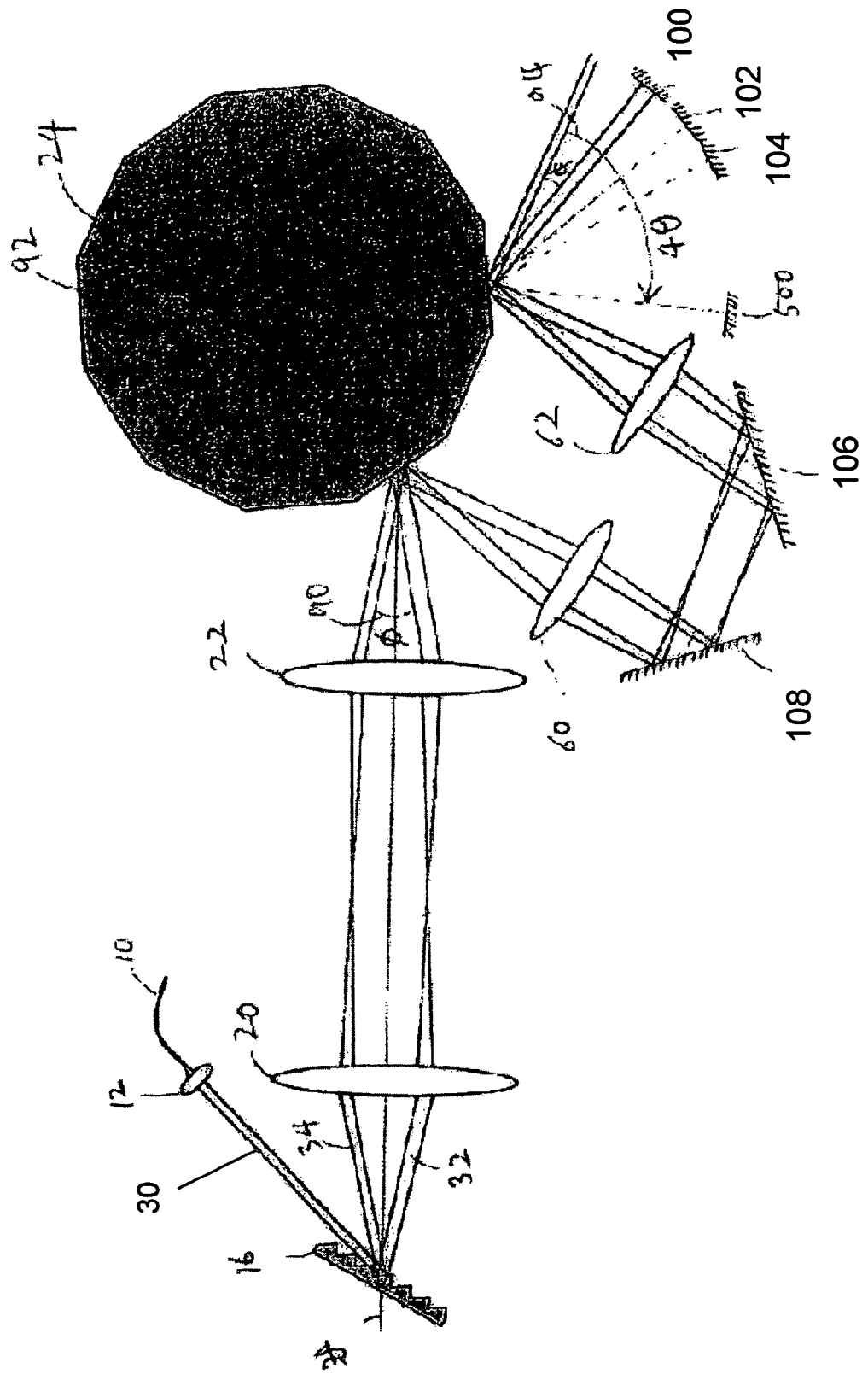
FIG. 1E is a block diagram of a fifth exemplary embodiment of the optical wavelength filter according to the present invention.

The filter tuning speed can be further increased by having the beam of light reflected multiple times by the polygon arrangement 24. A fifth exemplary embodiment of the present invention, depicted in FIG. 1E, is an arrangement for increasing the tuning speed by factor of 4K, where K is the ratio of angle 92 to angle 90 (K=θ/φ). The beam of light is reflected twice (e.g., four times round trip) by the polygon arrangement 24, so that the sweep angle 94 of the reflected light becomes angle 4θ, and the tuning speed becomes 4K times faster. Such reflection can also be assisted with the reflection of surfaces 100, 102, 104, 106 and 108. This exemplary embodiment of the filter arrangement can be used to broaden the free spectral range ("FSR") of the filter. For example, if one of the final reflectors 102 in the embodiment shown in FIG. 1E is removed, the FSR of the filter may become twice broader. It is likely that there is no tuning speed enhancement in such case. Similarly, it is possible to retain only one final reflector 100 in FIG. 1E. The FSR in this embodiment can become four times broader.

Figure 1F:
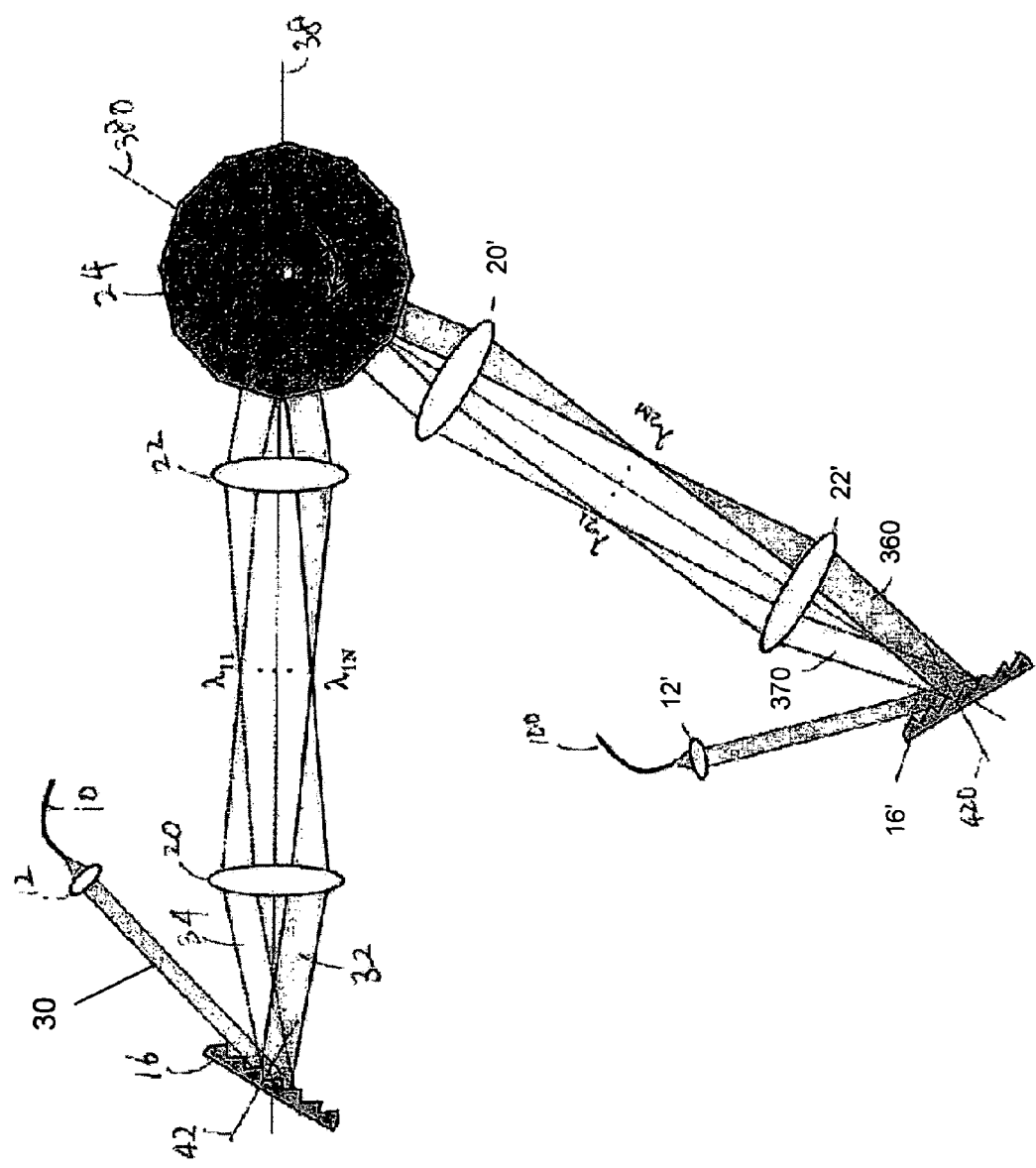
FIG. 1F is a block diagram of a sixth exemplary embodiment of the optical wavelength filter according to the present invention.

FIG. 1F shows a sixth exemplary embodiment of the present invention which provides a polygon tuning filter accommodating two light inputs and outputs. For example, in order to support two or more inputs and outputs of this filter, two or more sets of optical arrangements, each respective set including an input/output fiber 10, 10', a collimating lens 12, 12', a diffraction grating 16, 16', and a telescope, may share the same polygon arrangement 24. Because the scanning mirror of the polygon arrangement 24 is structurally isotropic about the rotation axis, certain optical arrangements that can deliver the beams of light to the polygon arrangement 24 can be accommodated from any directions. Since both sets of optical arrangement in the embodiment of FIG. 1F utilize the same polygon scanner, their respective scanning optical transmission spectra are synchronized. It should be understood that the exemplary embodiment of FIG. 1F can be extended to include multiple (greater than 2) optical arrangements each having its own input and output optical channel.

Figure 1G:
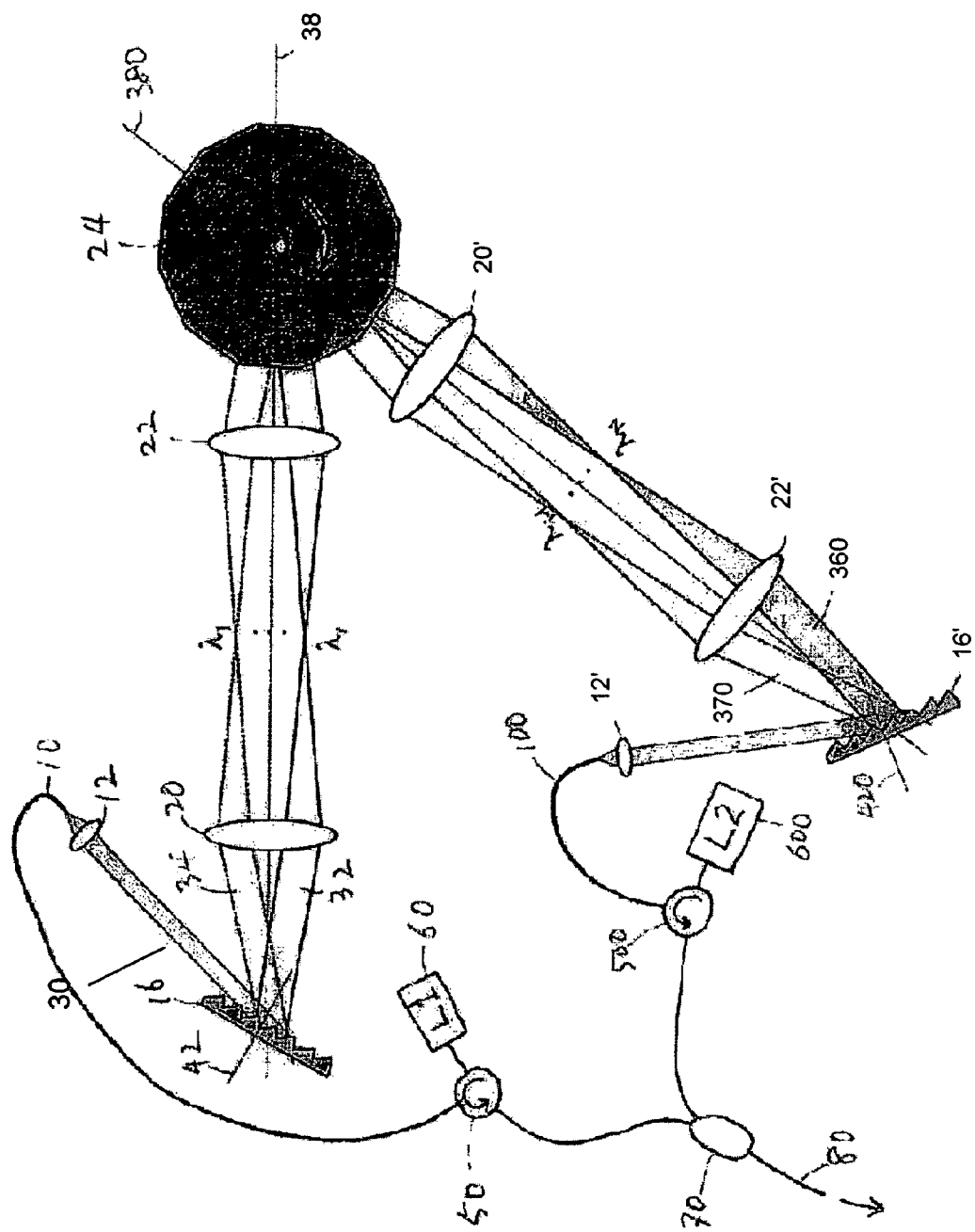
FIG. 1G is a block diagram of a seventh exemplary embodiment of the optical wavelength filter according to the present invention.

One exemplary application of the above-described polygon tuning filter according to the sixth embodiment of the present invention may be a wide band wavelength scanning light source. In FIG. 1G which shows a seventh exemplary embodiment of the present invention, a first broadband light source 60 provides a light signal which may have a wavelength $\lambda_1$ to $\lambda_i$, and a second broadband light source 600 provides another light signal having a wavelength $\lambda_{i-j}$ to $\lambda_N$. When the two optical arrangements supporting the wavelengths $\lambda_1$ to $\lambda_i$ and the wavelengths $\lambda_{i-j}$ to $\lambda_N$, respectively, are synchronized to output approximately the same wavelength at the same instance, such exemplary arrangement may become a wide band wavelength scanning light source with linear scan rate from $\lambda_i$ to $\lambda_N$. Since the FSR of the polygon scanning filter can be adjusted to be 200 nm or wider without any optical performance degradation, two or more broadband light sources with different center wavelengths can be combined with this filter to provide linear scanning light source over 200 nm tuning bandwidth. It should be understood that the embodiment of FIG. 1G can be extended to include multiple (e.g., greater than 2) optical arrangements and multiple (e.g., greater than 2) broadband light sources.

The exemplary embodiment illustrated in FIG. 1G can also be configured so that the wavelength tuning bands of each optical arrangement and broadband light source are discontinuous. In such a configuration, the tuning bands can be swept in a continuous or discontinuous sequential manner or be swept simultaneously.

Figure 2:
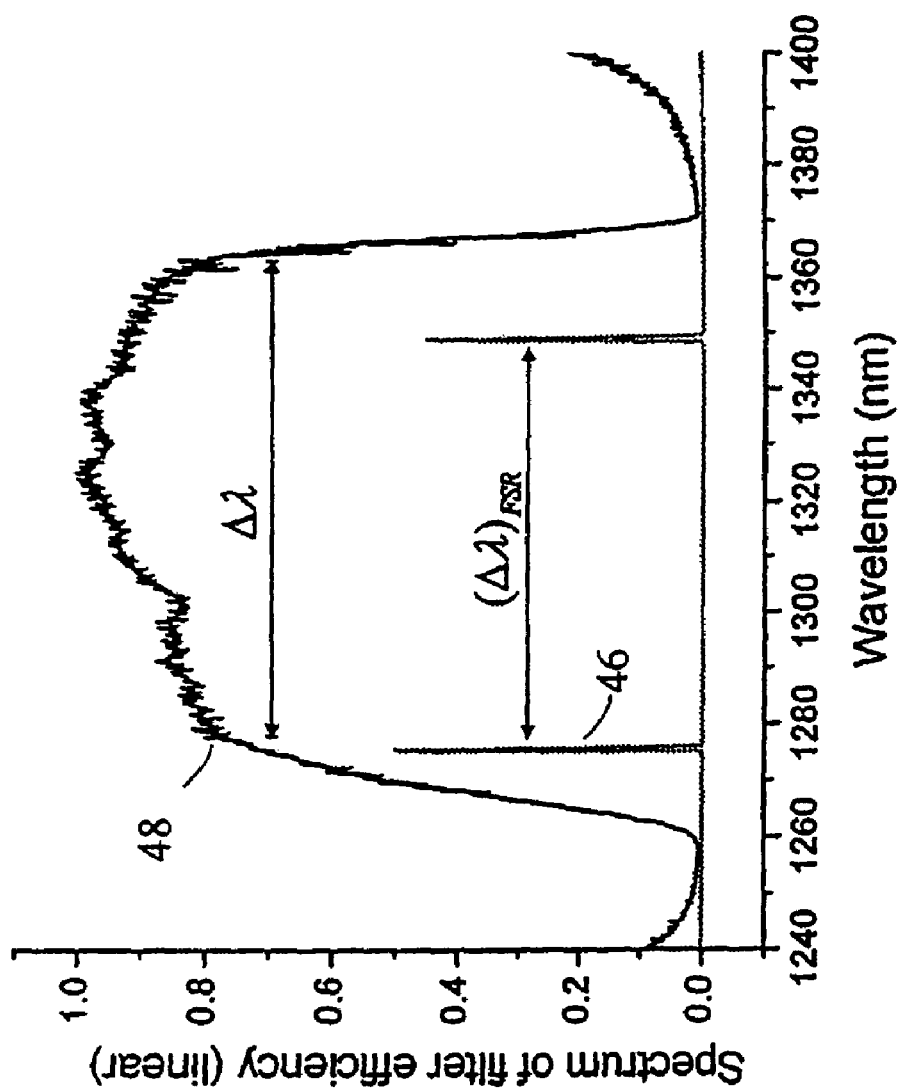
FIG. 2 is a graph of exemplary characteristics of the optical wavelength filter according to the present invention.

FIG. 2 shows an exemplary graph of measured characteristics of the filter according to an exemplary embodiment of the present invention. The normalized reflection spectrum of the filter, e.g., a curve 48, may be measured by using broadband amplifier spontaneous emission light from a semiconductor optical amplifier (SOA) and an optical spectrum analyzer. The optical spectrum analyzer can obtain or record a normalized throughput (reflected) spectrum in peak-hold mode while the polygon arrangement 24 spins at its maximum speed of 15.7 kHz. The measured tuning range may be 90 nm which is substantially smaller than the theoretical value of 126 nm. It is possible to have a discrepancy which may be due to an aberration of the telescope 6', primarily field curvature, associated with relatively large angular divergence of the beam from the grating. Such aberration can be corrected using optimized lens designs well known in the art. A curve 46 shown in FIG. 2 illustrates the throughput spectrum when the polygon arrangement is static at a particular position. The observed free spectral range is 73.5 nm, in agreement with a theoretical calculation. The FWHM bandwidth of curve 46 was measured to be 0.12 nm. The discrepancy between the measured FWHM and the theoretical limit of 0.09 nm is reasonable considering the aberration and imperfection of the optical elements.

Figure 3:
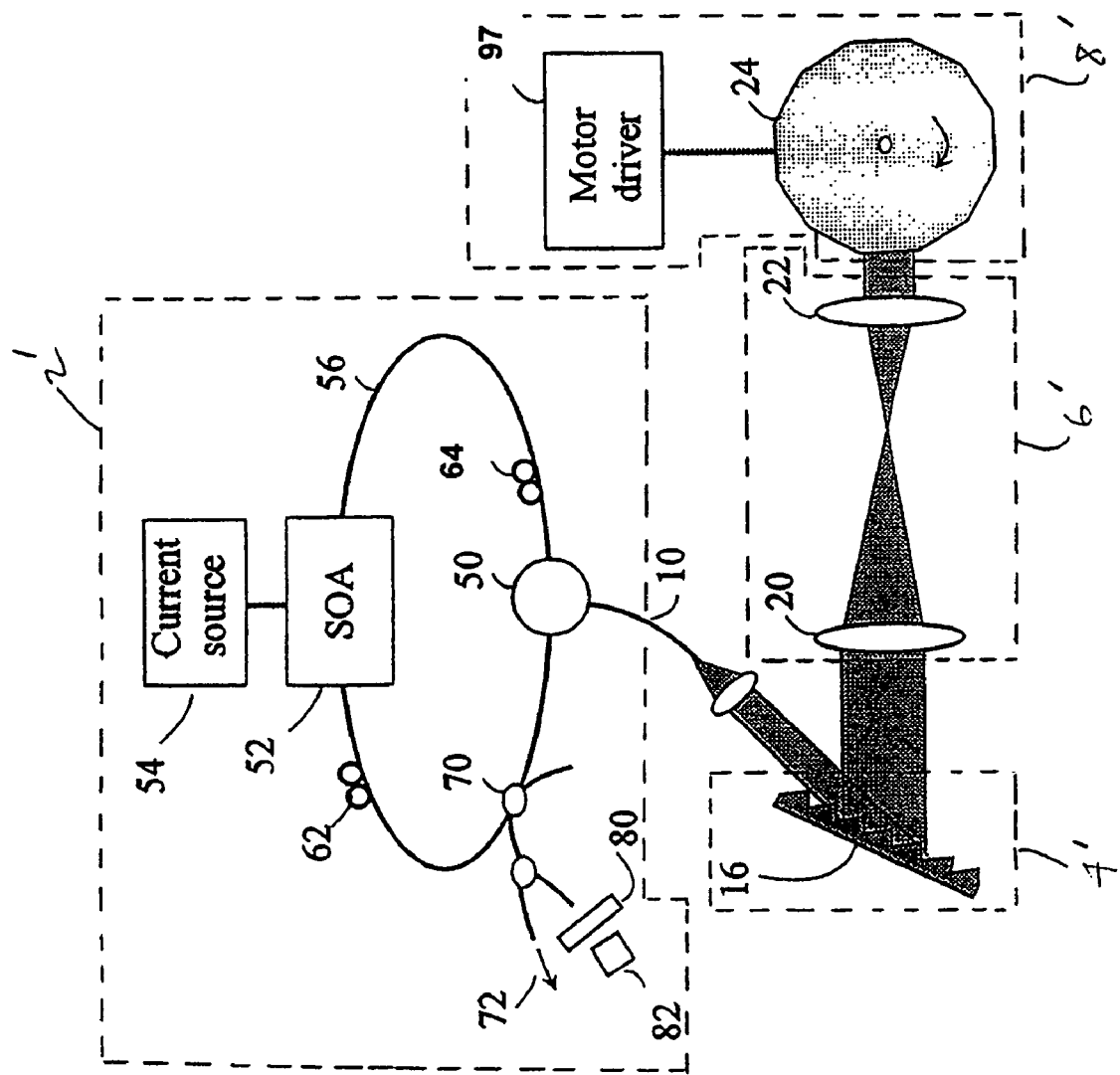
FIG. 3 in as illustration of an exemplary embodiment of a wavelength tuning laser source according to the present invention.

FIG. 3 shows an exemplary embodiment of the wavelength tuning laser source according to the present invention. For example, the polygon-based filter can be incorporated into an extended-cavity semiconductor laser via a Faraday circulator 50. Intra-cavity elements may be connected by single-mode optical fibers 10. The gain medium may be a semiconductor optical amplifier 52 (e.g., SOA, Philips, CQF 882/e). Laser output 72 may be obtained via the 90% port of a fiber-optic fused coupler 70. Two polarization controllers 64, 62 can be used to align the polarization states of the intra-cavity light to the axes of maximum efficiency of the grating 16, and of the maximum gain of the SOA 50. A current source 54 may provide an injection current to the SOA 50. The polygon arrangement 24 may be driven and controlled by a motor driver 97. To generate a sync signal useful for potential applications, approximately 5% of the laser output may be directed to a photodetector 82 through a variable wavelength filter 80 with bandwidth of 0.12 nm. In this exemplary implementation, the center wavelength of the filter was fixed at 1290 nm. The detector signal can generate short pulses when the output wavelength of the laser is swept through the narrow passband of the fixed-wavelength filter. The timing of the sync pulse may be controlled by changing the center wavelength of the filter.

Figure 4A:
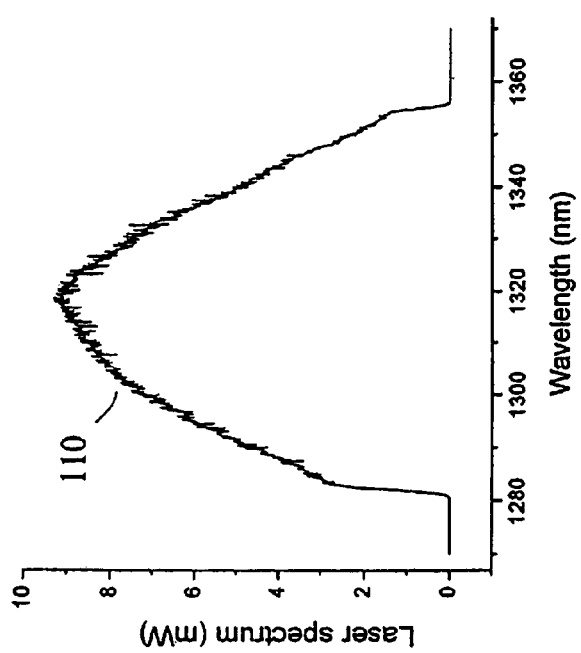
FIG. 4A is a graph of exemplary first output characteristics (laser spectrum vs. wavelength) of the laser source according to the present invention.
Figure 4B:
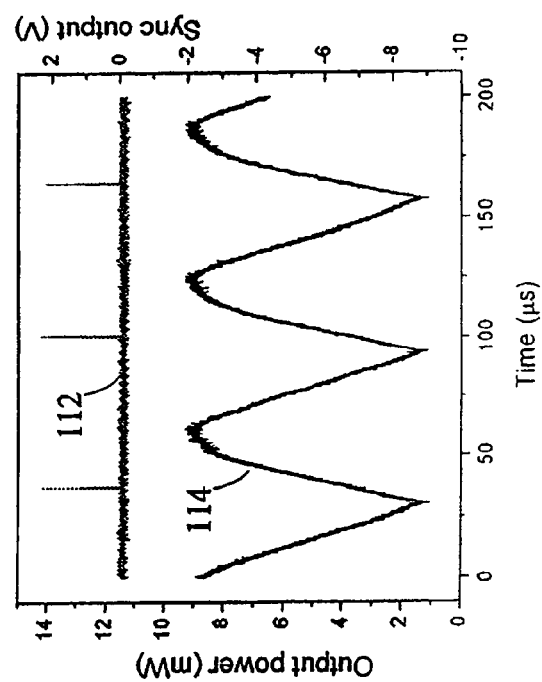
FIG. 4B is a graph of exemplary second output characteristics (output power vs. time) of the laser source according to the present invention.

FIG. 4A shows a graph of exemplary first output characteristics (laser spectrum vs. wavelength) of the laser source according to the present invention, and FIG. 4B is a graph of exemplary second output characteristics (output power vs. time) of the laser source according to the present invention. Turning to FIG. 4A, curve 110 represents the output spectrum of the laser measured by the optical spectrum analyzer in peak-hold mode, e.g., when the polygon arrangement spins at 15.7 kHz. The edge-to-edge sweep range was observed to be from 1282 nm to 1355 nm, equal to the free-spectral range of the filter. The Gaussian-like profile of the measured spectrum, rather than a square profile, can be mainly due to the polarization-dependent cavity loss caused by polarization sensitivity of the filter and the birefringence in the cavity. It may be preferable to adjust the polarization controllers to obtain the maximum sweep range and output power. In FIG. 4B, curve 114 is the output of the exemplary laser in the time domain. The upper trace 112 is the sync signal which may be obtained through the fixed-wavelength filter. The amplitude of power variation from facet to facet was less than 3.5%. The peak and average output power was 9 mW and 6 mW, respectively. The y-axis scale of the curve 110 of FIG. 4A can be calibrated from the time-domain measurement, because the optical spectrum analyzer records a time-averaged spectrum due to the laser tuning speed being much faster than the sweep speed of the spectrum analyzer.

Figure 5:
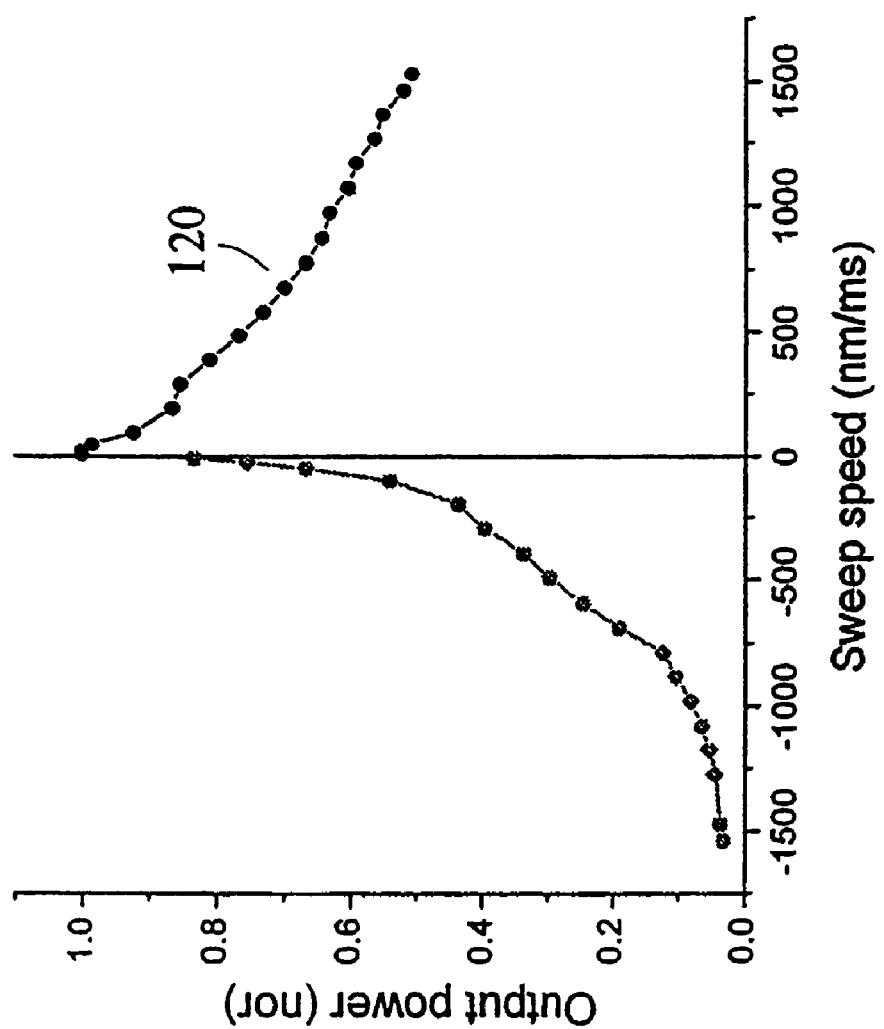
FIG. 5 is a graph of exemplary output power provided as a function of sweep speed according to the present invention.

A frequency downshift in the optical spectrum of the intracavity laser light may arise as the light passes through the SOA gain medium, as a result of an intraband four-wave mixing phenomenon. In the presence of the frequency downshift, greater output power can be generated by operating the wavelength scanning filter in the positive wavelength sweep direction. FIG. 5 shows an exemplary illustration of a normalized peak power of the laser output measured as a function of the tuning speed. The negative tuning speed can be obtained by flipping the position of the collimator and the orientation of the grating with respect to the optic axis 38 of the exemplary embodiment of the arrangement according to the present invention. It is preferable to make the physical parameters of the filter identical in both tuning directions. The result shows that the combined action of self-frequency shift and positive tuning allows higher output to be obtained and enables the laser to be operated at higher tuning speed as is demonstrated in the curve 120. Therefore, the positive wavelength scan may be the preferable operation. The output power can be decreased with an increasing tuning speed. A short cavity length may be desired to reduce the sensitivity of the output power to the tuning speed. In such case, a free-space laser cavity may be preferred.

Figure 6:
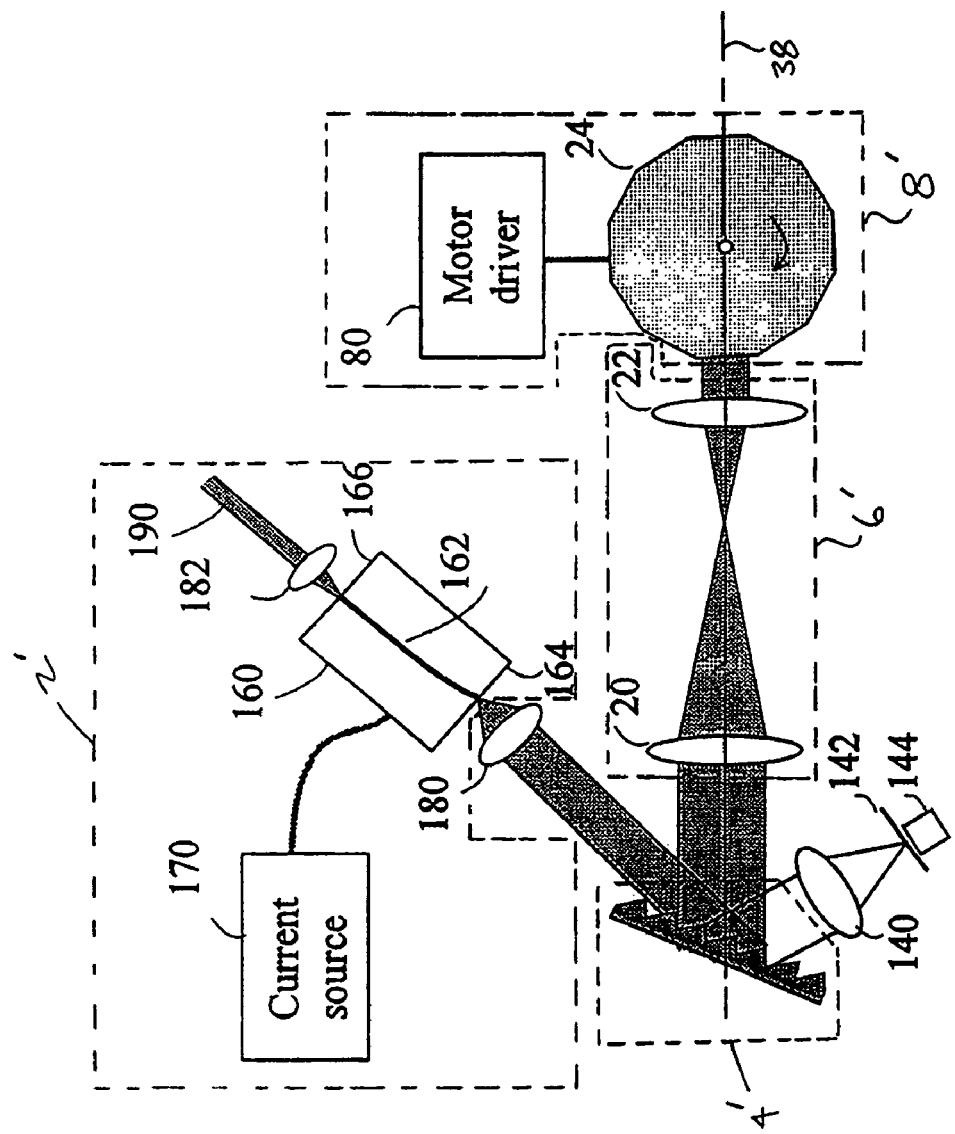
FIG. 6 is an exemplary embodiment of a free-space extended-cavity semiconductor tunable laser arrangement according to the present invention.

An exemplary embodiment of a free-space extended-cavity semiconductor tunable laser arrangement according to the present invention is depicted in FIG. 6. A semiconductor waveguide 162 made on a substrate chip 160 can be coupled to the polygon scanning filter via a collimating lens 180. The front facet 164 thereof may be anti-reflection coated, and the output facet 166 may be cleaved or preferably coated with dielectrics to have an optimal reflectivity. The laser output 190 may be obtained through the output coupling lens 182. The sync output may be taken by using a lens 140, a pinhole 142, and a photodetector 144 positioned on the 0-th order diffraction path for the light which is on retro-reflection from the polygon scanner 24. The photodetector 144 can generate a short pulse when the focus of the optical beam of a particular wavelength sweeps through the pinhole 142. Other types of gain medium include but are not limited to rare-earth-ion doped fiber, Ti:Al$_2$O$_3$, and Cr$^{3+}$:forsterite. The first and second lenses 20, 22 can be preferably achromats with low aberration particularly in field curvature and coma. The collimating lenses 180, 182 are preferably aspheric lenses.

Figure 7:
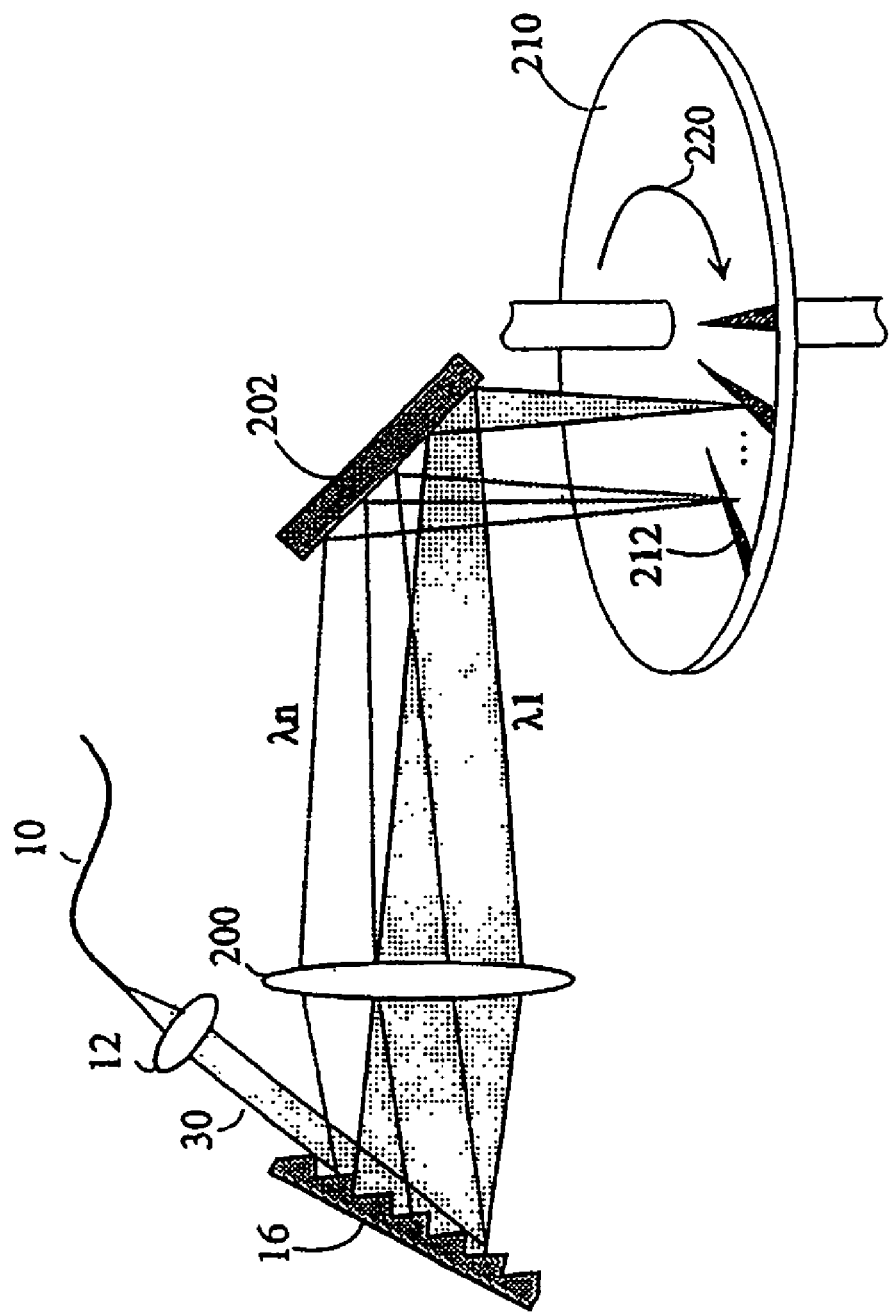
FIG. 7 is an illustration of a seventh exemplary embodiment of the optical wavelength filter according to the present invention.

FIG. 7 shows another exemplary embodiment of the wavelength tunable filter which includes an input collimating lens 12, diffraction grating 16, focusing lens 200, and a spinning disk 210, as shown in FIG. 7. The diffraction grating 16 preferably has a concave curvature that has a focal length and may thus eliminate the need for the use of the focusing lens 200. The diffraction grating may be replaced by other angular dispersive elements such as a prism. Preferably more than one reflector 212 can be deposited on the surface of the spinning disk 210. Preferably, the reflectors 212 may include multiple narrow stripes periodically and radially patterned. The material for the reflectors is preferably gold. The disk 210 can be made of a lightweight plastic or silicon substrate. Instead of the reflectors deposited on the top surface of the disk, the disk can have a series of through holes followed by a single reflector attached to the back surface of the disk or supported independently from the disk. Incident from the optical fiber 10, the optical beams of different wavelengths are illuminated on the surface of the disk into a line after being diffracted by the grating 16 and focused by the lens 200. The beam that hits the reflectors of the spinning disk may be retro-reflected and received by the optical fiber 10. For example, a mirror 202 may be used to facilitate the access of the beam onto the disk.

The distance from the lens 200 to the reflectors of the disk 210 may be approximately equal to the focal length, F, of the lens 200. The tuning range of the filter may be given by $\Delta\lambda = p \cos \beta_0 (D/F)$, where D denotes the distance between the stripes. The width of the strip, w, can preferably be substantially equal to the beam spot size, $w_s$, at the surface of the disk:

$$w_s = W \frac{\cos\beta_0}{\cos\alpha} \cdot \frac{F/z}{\sqrt{1+f/z^2}},$$

where $z=\pi w_s^2/\lambda$. Such formulation may lead to a FWHM filter bandwidth given by $(\delta\lambda)_{FWHM}/\lambda_0 = A \cdot (p/m) \cos \alpha/W$ where $A=\sqrt{4\ln 2}/\pi$. For $w>w_s$, the filter bandwidth may become greater, and for $w<w_s$, the efficiency (reflectivity) of the filter can be decreased by beam clipping. The orientation of the incident beam 30 with respect to the optic axis of the lens 200 and the spinning direction 220 may determine the sense of wavelength tuning. The positive wavelength scan may be preferable, which is the case of the exemplary embodiment shown in FIG. 7.

Figure 8:
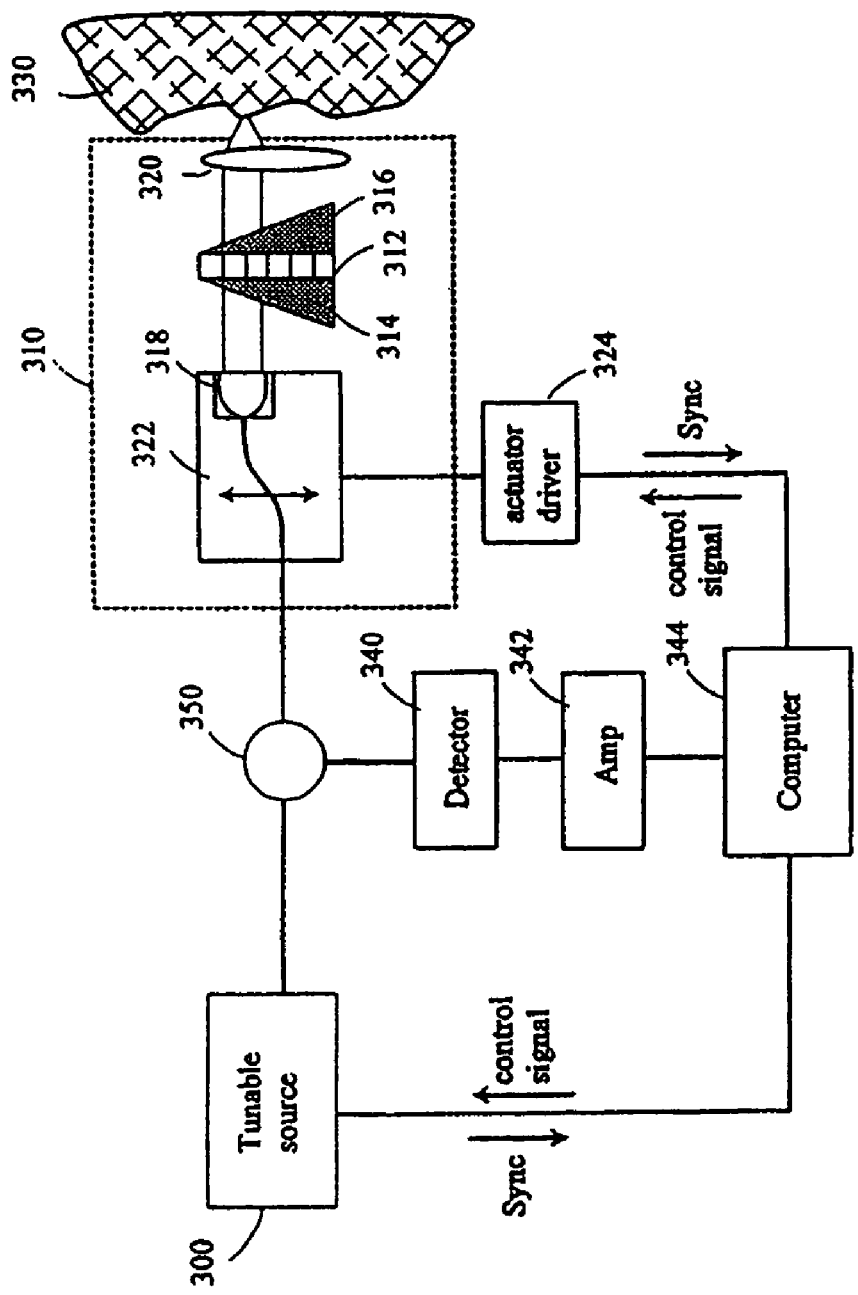
FIG. 8 is a schematic diagram of an exemplary embodiment of a spectrally-encoded confocal microscope that utilizes the tunable laser source according to the present invention.

Two exemplary applications of the exemplary embodiments of the present invention are described as follows. FIG. 8 shows a block diagram of an exemplary embodiment of the spectrally encoded confocal microscope ("SECM") that uses the aforementioned tunable laser source 300. The basic principle of SECM has been described in detail in U.S. Pat. No. 6,341,036, the disclosure of which is incorporated herein by reference in its entirety. An exemplary probe 310 includes a transmission grating 312 provided between two silicon prisms 314, 316, a collimator 318, and a microscope objective lens 320. The probe is equipped with a micro actuator 322 to scan the beam onto a different location of the sample 330. The actuator 322 may be driven by an actuator driver 324 at substantially slower speed than the tuning speed of the laser source. The probe motion is preferably rotary or translational and is synchronized to the sync output of the laser source. In one example, the wavelength sweep frequency may be 15.7 kHz, and the probe scan frequency can be 30 Hz, which allows 30 frames of image to be obtained in 1 second. The objective lens 320 has a nigh numerical aperture to provide a transverse resolution of an order of micrometers and a confocal parameter of a few micrometers. The focus of the optical beam may be continuously scanned in time over the sample 330 by the swept output wavelength of the optical source and the scanning motion of the probe. The optical power returned from the sample is proportional to the reflectivity of the sample within a small section where the beam was focused down to a narrow waist at a given time. Two dimensional en-face image of the sample is constructed by a signal processor 344. The detector 340 is preferably an avalanche photodiode ("APD") followed by a transimpedance amplifier 342. The reflected power may be received through a Faraday circulator 350 or a fiber-optic coupler.

Figure 9:
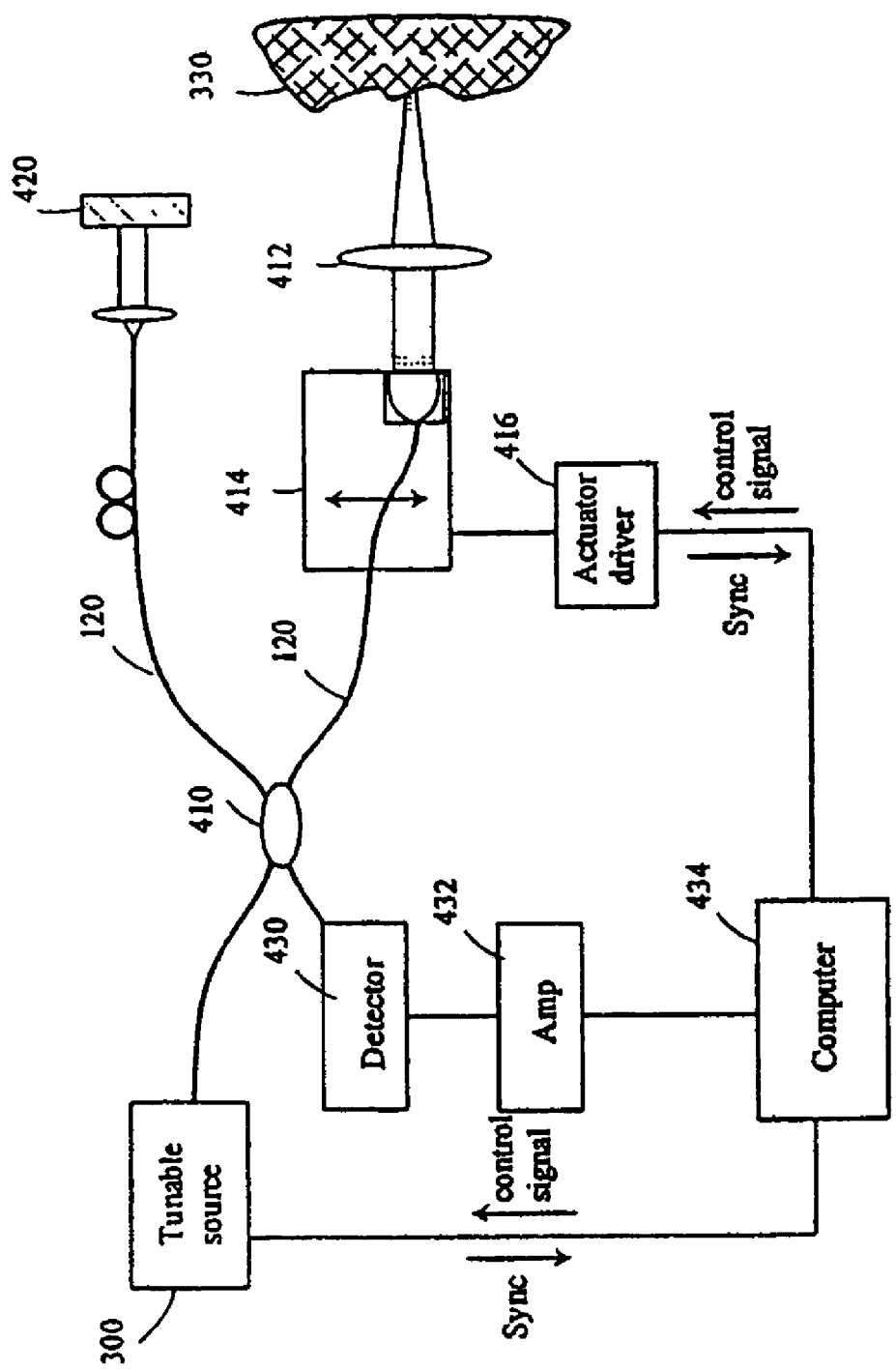
FIG. 9 is a schematic diagram of an exemplary embodiment of a frequency-domain optical coherence tomography arrangement that utilizes the tunable laser source according to the present invention.

Another exemplary application of the exemplary embodiments of the present invention is for optical coherence tomography ("OCT") the details of which are described in U.S. Pat. No. 5,956,355, the disclosure of which is incorporated herein by reference in its entirety. In one exemplary configuration, depicted in FIG. 9, an output of a tunable source 300 may be directed to a sample 330 through a fiber-optic coupler 410. An objective lens 412 in the probe may typically provide a focus near the surface or within the sample 330. The reference mirror 420 can be placed in a reference arm 120 at a position where an optical path length between two arms of the Michelson interferometer is substantially matched. Alternatively, the reference path can be configured in a transmissive, non-reflective configuration. The detector 430 may be a PIN photodiode followed by a transimpedance amplifier 432 with finite frequency bandwidth. The detector may preferably incorporate polarization diverse and dual balanced detection. The detector signal can be processed in the processor 434 through a fast Fourier transform to construct the depth image of the sample. The probe may be scanned by an actuator 414 and an actuator driver 416 to allow a 3-dimensional image of the sample to be obtained.

Figure 10B:
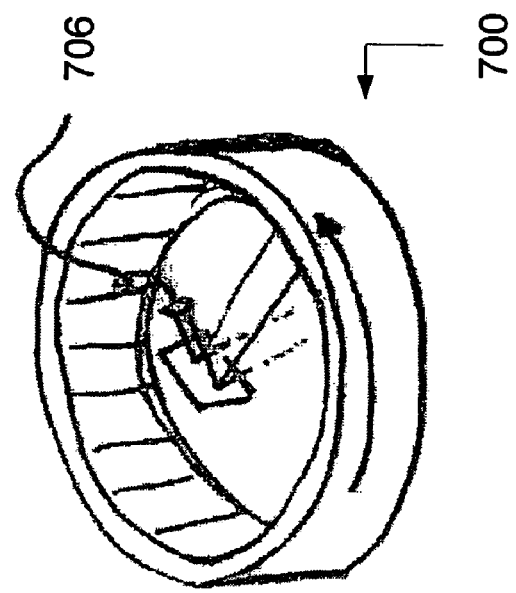
FIG. 10B is a perspective plan view of the wavelength filter shown in FIG. 10A.
Figure 10A:
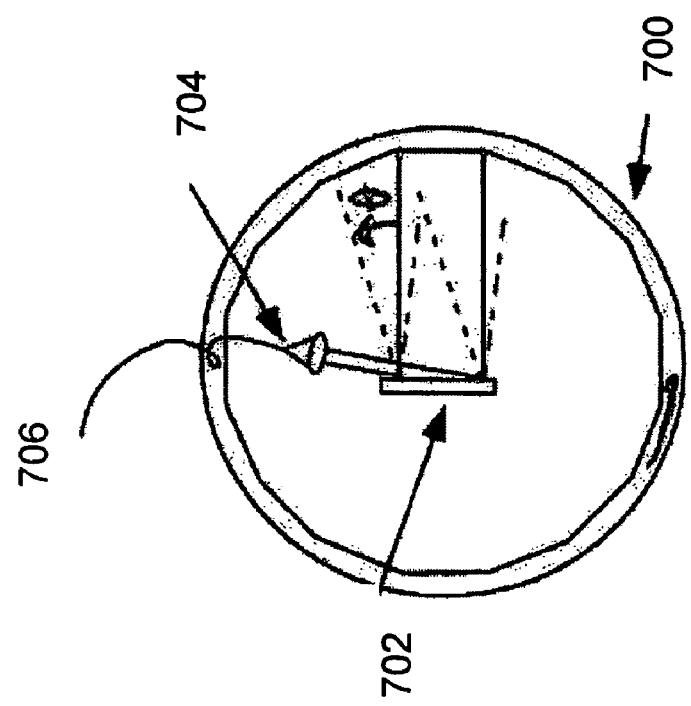
FIG. 10A is a top view of an eighth exemplary embodiment of the wavelength filter according to the present invention.

FIGS. 10A and 10B show a top and perspective view of another exemplary embodiment of the wavelength tunable filter according to the present invention. An angularly deflecting optical element 700 of this exemplary embodiment can be a rotating polygon arrangement 24 where the facets of the polygon are on the inner diameter of a hollow cylinder. A dispersing element 702 such as a diffraction grating can be placed at the center of the polygon arrangement 24. Light can be delivered to the grating through an optical fiber and collimated onto the grating so that each frequency component of the light is diffracted through a different angle (Θ). Only one narrow range of frequencies may be substantially orthogonal to one facet of the polygon arrangement 24, and therefore such frequency range may be reflected back to the diffraction grating and collected by the optical fiber 704/706. When the cylinder rotates, a surface normal direction for the illuminated polygon arrangement's facet may align with a new narrow frequency range. By rotating the cylinder, frequency tuning can thereby be achieved. When the cylinder rotation angle becomes large, an adjacent facet of the polygon arrangement 24 can become aligned with the light diffracted from the grating and the filter will repeat another frequency tuning cycle. The free spectral range and finesse can be controlled by appropriate choice of the polygon diameter, number of facets, collimated beam diameter and diffraction grating groove density.

The foregoing merely illustrates the principles of the invention. Various modifications and alterations to the described embodiments will be apparent to those skilled in the art in view of the teachings herein. For example, the invention described herein is usable with the exemplary methods, systems and apparatus described in U.S. patent application No. 60/514,769. It will thus be appreciated that those skilled in the art will be able to devise numerous systems, arrangements and methods which, although not explicitly shown or described herein, embody the principles of the invention and are thus within the spirit and scope of the present invention.

What is claimed is:

1. An apparatus for filtering an electromagnetic radiation comprising:
    at least one spectral separating arrangement configured to angularly separate one or more components of the electromagnetic radiation based on a frequency of the electromagnetic radiation;
    at least one angularly deflecting optical arrangement that includes a pivot point, and configured to receive the one or more components of the electromagnetic radiation to generate at least one signal associated with the one or more components; and
    at least one optical imaging arrangement configured to directly receive from the spectral separating arrangement the one or more components of the electromagnetic radiation, and generate an image of one or more dispersive elements of the at least one spectral separating arrangement associated with the one or more components toward the deflecting optical arrangement.

2. The apparatus according to claim 1, wherein a deflection point of the angularly deflecting optical element substantially overlaps with a real image of at least one of the dispersive elements.

3. The apparatus according to claim 2, further comprising at least one reflector which is configured to receive at least one signal from the at least one angularly deflecting optical arrangement.

4. The apparatus according to claim 1, wherein the at least one of the dispersive elements is at least one of a diffraction grating, a prism, a grism, an acousto-optic beam deflector, a virtual phased array, and an arrayed waveguide grating.

5. The apparatus according to claim 1, wherein the at least one angularly deflecting optical element is at least one of a polygon mirror scanner, a galvanometer mirror scanner, and a piezo-electric mirror scanner.

6. The apparatus according to claim 1, further comprising at least one beam selecting arrangement adapted to receive the at least one signal, and selectively generate at least one selected signal.

7. The apparatus according to claim 1, wherein the at least one spectral separating arrangement is configured to (i) receive the electromagnetic radiation which has multiple wavelengths, and (ii) generate a multiple of the one or more components, each of which having a respective one of the multiple wavelengths and each being provided at a different angle.

8. An apparatus for filtering an electromagnetic radiation, comprising:
    at least one spectral separating arrangement configured to angularly separate one or more components of the electromagnetic radiation based on a frequency of the electromagnetic radiation;
    at least one angularly deflecting optical arrangement that includes a pivot point, and configured to receive the one or more components of the electromagnetic radiation to generate at least one signal associated with the one or more components; and
    at least one optical imaging arrangement configured to receive the one or more components of the electromagnetic radiation, and generate an image of one or more dispersive elements associated with the one or more components; and at least one beam selecting arrangement adapted to receive the at least one signal, and selectively generate at least one selected signal, wherein a position of the pivot point is provided in a proximity of at least one of (i) a virtual image of at least one of the dispersive elements of the spectral separating arrangement, or (ii) a real image of at least one of the dispersive elements of the spectral separating arrangement.

9. A source arrangement for providing an electromagnetic radiation, comprising:

at least one emitter of the electromagnetic radiation;

at least one spectral separating arrangement configured to angularly separate one or more components of the electromagnetic radiation based on a frequency of the electromagnetic radiation;

at least one angularly deflecting optical arrangement that includes a pivot point, and configured to receive the one or more components of the electromagnetic radiation to generate at least one signal associated with the one or more components; and at least one optical imaging arrangement configured to directly receive from the spectral separating arrangement the one or more components of the electromagnetic radiation, and generate an image of one or more dispersive elements of the spectral separating arrangement associated with the one or more components toward the deflecting optical arrangement.

10. The source arrangement according to claim 9, wherein the at least one emitter is at least one of a semiconductor optical amplifier, a laser diode, a super-luminescent diode, a doped optical fiber, a doped laser crystal, a doped laser glass, and a laser dye.

11. The source arrangement according to claim 9, further comprising at least one beam selecting arrangement adapted to receive the at least one signal, and selectively generate at least one selected signal.

12. The source arrangement according to claim 9, wherein the at least one spectral separating arrangement is configured to (i) receive the electromagnetic radiation which has multiple wavelengths, and (ii) generate a multiple of the one or more components, each of which having a respective one of the multiple wavelengths and each being provided at a different angle.

13. A source arrangement for providing an electromagnetic radiation, comprising:

at least one laser gain medium providing the electromagnetic radiation;

at least one spectral separating arrangement configured to angularly separate one or more components of the electromagnetic radiation based on a frequency of the electromagnetic radiation;

at least one angularly deflecting optical arrangement that includes a pivot point, and configured to receive the one or more components of the electromagnetic radiation to generate at least one signal associated with the one or more components;

at least one beam selecting arrangement adapted to receive the at least one signal, and selectively generate at least one selected signal; and at least one optical imaging arrangement configured to directly receive from the spectral separating arrangement the one or more components of the electromagnetic radiation, and generate an image of one or more dispersive elements of the spectral separating arrangement associated with the one or more component toward the deflecting optical arrangement.

14. The source arrangement according to claim 13, further comprising at least one laser cavity receiving the electromagnetic radiation.

15. The source arrangement according to claim 14, wherein the laser cavity is a ring laser cavity.

16. The source arrangement according to claim 13, wherein the laser gain medium is at least one of a semiconductor optical amplifier, a laser diode, a super-luminescent diode, a doped optical fiber, a doped laser crystal, a doped laser glass, and a laser dye.

17. The source arrangement according to claim 13, wherein the at least one spectral separating arrangement provides a frequency sweep continuously in a positive wavelength direction.

18. The source arrangement according to claim 13, further comprising an optical circulator.

19. The source arrangement according to claim 13, wherein wavelength ranges of the at least one laser gain media are not identical to one another.

20. The source arrangement according to claim 13, further comprising at least one beam selecting arrangement adapted to receive the at least one signal, and selectively generate at least one selected signal.

21. The source arrangement according to claim 13, wherein the at least one spectral separating arrangement is configured to (i) receive the electromagnetic radiation which has multiple wavelengths, and (ii) generate a multiple of the one or more components, each of which having a respective one of the multiple wavelengths and each being provided at a different angle.

22. An apparatus for filtering an electromagnetic radiation comprising:

at least one spectral separating arrangement configured to angularly separate one or more components of the electromagnetic radiation based on a frequency of the electromagnetic radiation;

at least one angularly deflecting optical arrangement that includes a pivot point, and configured to receive the one or more components of the electromagnetic radiation to generate at least one signal associated with the one or more components; and at least one optical imaging arrangement configured to directly receive from the spectral separating arrangement the one or more components of the electromagnetic radiation, and converge and project the one or more components of the electromagnetic radiation onto an image plane.

23. A source arrangement for providing an electromagnetic radiation, comprising:

at least one emitter of the electromagnetic radiation;

at least one spectral separating arrangement configured to angularly separate one or more components of the electromagnetic radiation based on a frequency of the electromagnetic radiation;

at least one angularly deflecting optical arrangement that includes a pivot point, and configured to receive the one or more components of the electromagnetic radiation to generate at least one signal associated with the one or more components; and at least one optical imaging arrangement configured to directly receive from the spectral separating arrangement the one or more components of the electromagnetic radiation, and converge and project the one or more components of the electromagnetic radiation onto an image plane.

24. A source arrangement for providing an electromagnetic radiation, comprising:
- at least one laser gain medium providing the electromagnetic radiation;
- at least one spectral separating arrangement configured to angularly separate one or more components of the electromagnetic radiation based on a frequency of the electromagnetic radiation;
- at least one angularly deflecting optical arrangement that includes a pivot point, and configured to receive the one or more components of the electromagnetic radiation to generate at least one signal associated with the one or more components;
- at least one beam selecting arrangement adapted to receive the at least one signal, and selectively generate at least one selected signal; and
- at least one optical imaging arrangement configured to directly receive from the spectral separating arrangement the one or more components of the electromagnetic radiation, and converge and project the one or more components of the electromagnetic radiation onto an image plane.

* * * * *

UNITED STATES PATENT AND TRADEMARK OFFICE
CERTIFICATE OF CORRECTION

PATENT NO. : 7,519,096 B2  
APPLICATION NO. : 10/861179  
DATED : April 14, 2009  
INVENTOR(S) : Brett Eugene Bouma et al.

Page 1 of 1

It is certified that error appears in the above-identified patent and that said Letters Patent is hereby corrected as shown below:

Col. 1 lines 12-19  
Modify the "Statement Regarding Federally Sponsored Research" section with the following paragraph as follows:

"This invention was made with Government support under Grant No. DAMD17-02-2-0006 awarded by the U.S. Department of the Army and Grant No. BES-0086709 awarded by the National Science Foundation. Thus, the Government has certain rights in this invention"

Signed and Sealed this  
Twenty-eighth Day of February, 2012

David J. Kappos  
*Director of the United States Patent and Trademark Office*